(12) United States Patent
Wright

(10) Patent No.: US 8,935,101 B2
(45) Date of Patent: Jan. 13, 2015

(54) METHOD AND APPARATUS FOR CORRELATING PRECURSOR AND PRODUCT IONS IN ALL-IONS FRAGMENTATION EXPERIMENTS

(75) Inventor: David A. Wright, Livermore, CA (US)

(73) Assignee: Thermo Finnigan LLC, San Jose, CA (US)

( * ) Notice: Subject to any disclaimer, the term of this patent is extended or adjusted under 35 U.S.C. 154(b) by 922 days.

(21) Appl. No.: 12/970,570

(22) Filed: Dec. 16, 2010

(65) Prior Publication Data

US 2012/0158318 A1    Jun. 21, 2012

(51) Int. Cl.
| | |
|---|---|
| *G01N 30/72* | (2006.01) |
| *G06F 17/40* | (2006.01) |
| *G06F 19/00* | (2011.01) |
| *B01D 59/44* | (2006.01) |
| *G01N 15/02* | (2006.01) |
| *G01N 30/86* | (2006.01) |

(52) U.S. Cl.
CPC ............ *G01N 30/8675* (2013.01); *G01N 15/02* (2013.01); *G01N 30/72* (2013.01); *B01D 59/44* (2013.01); *G06F 19/703* (2013.01); *G06F 17/40* (2013.01); *G06F 19/00* (2013.01); *G01N 30/7266* (2013.01); *G01N 30/8637* (2013.01); *G01N 30/8641* (2013.01); *G01N 30/8686* (2013.01)
USPC ............... 702/27; 73/866; 250/281; 430/173; 702/1; 702/32; 702/127; 702/187; 702/189

(Continued)

(58) Field of Classification Search
CPC .......... B01D 59/00; B01D 59/44; G01D 7/00; G01D 9/00; G01D 21/00; G01N 15/00; G01N 15/02; G01N 23/00; G01N 30/00; G01N 30/02; G01N 30/62; G01N 30/72; G01N 30/7233; G01N 30/724; G01N 30/7266; G01N 30/86; G01N 30/8624; G01N 30/8631; G01N 30/8637; G01N 30/8641; G01N 30/8675; G01N 30/8686; G01N 30/88; G01N 30/96; G01N 2030/00; G01N 2030/02; G01N 2030/86; G01N 2030/8624; G01N 2030/8648; G01N 2030/96; G06F 11/00; G06F 11/30; G06F 11/32; G06F 11/34; G06F 17/00; G06F 17/40; G06F 19/00; H01J 19/00; H01J 49/00; H01J 49/04; H01J 49/26
USPC ............. 73/19.01, 19.02, 23.2, 23.35, 23.36, 73/23.37, 432.1, 865.5, 865.8, 866, 866.3; 250/281, 282, 283, 306, 307; 378/1, 378/162; 430/173; 702/1, 22, 23, 26, 27, 702/28, 30, 32, 127, 187, 189, 190; 708/100, 105, 200
IPC ............. B01D 59/00, 59/44; G01D 7/00, 9/00, G01D 21/00; G01N 15/00, 15/02, 30/00, G01N 30/02, 30/62, 30/72, 30/7233, 30/724, G01N 70/7266, 30/86, 30/8624, 30/8631, G01N 30/8637, 30/8641, 30/86725, 30/8686, G01N 30/88, 30/96, 2030/00, 2030/02, 2030/86, G01N 2030/8624, 2030/8648, 2030/96; G06F 11/00, 11/30, 11/32, 11/34, 17/00, 17/40, G06F 19/00; H01J 19/00, 49/00, 49/004, H01J 49/26
See application file for complete search history.

(56) References Cited

U.S. PATENT DOCUMENTS

| | | | |
|---|---|---|---|
| 4,353,242 A | 10/1982 | Harris et al. | |
| 4,694,168 A * | 9/1987 | Le Beyec et al. | 250/287 |
| 5,073,713 A | 12/1991 | Smith et al. | |
| 5,453,613 A | 9/1995 | Gray et al. | |
| 5,672,869 A | 9/1997 | Windig et al. | |
| 5,886,346 A | 3/1999 | Makarov | |
| 6,107,623 A | 8/2000 | Bateman et al. | |
| 6,329,652 B1 | 12/2001 | Windig et al. | |
| 6,444,979 B1 | 9/2002 | Watanabe | |
| 6,518,568 B1 * | 2/2003 | Kovtoun et al. | 250/287 |
| 6,581,013 B1 | 6/2003 | Annis et al. | |
| 6,717,130 B2 | 4/2004 | Bateman et al. | |

| | | | |
|---|---|---|---|
| 6,745,133 | B2 | 6/2004 | Axelsson |
| 6,872,938 | B2* | 3/2005 | Makarov et al. ............... 250/281 |
| 6,873,915 | B2 | 3/2005 | Hastings |
| 6,982,414 | B2* | 1/2006 | Bateman et al. ............... 250/282 |
| 7,056,434 | B2 | 6/2006 | Van Der Greef et al. |
| 7,141,784 | B2 | 11/2006 | Vachet et al. |
| 7,158,862 | B2 | 1/2007 | Liebler et al. |
| 7,197,401 | B2 | 3/2007 | Hastings |
| 7,297,941 | B2 | 11/2007 | Senko et al. |
| 7,345,275 | B2* | 3/2008 | Amirav et al. ................ 250/282 |
| 7,457,708 | B2 | 11/2008 | Thompson et al. |
| 7,488,935 | B2 | 2/2009 | Altmayer |
| 7,606,667 | B2 | 10/2009 | Herold et al. |
| 7,800,055 | B2 | 9/2010 | Geromanos et al. |
| 7,983,852 | B2* | 7/2011 | Wright et al. .................... 702/32 |
| 7,996,156 | B2* | 8/2011 | Beger et al. ..................... 702/19 |
| 8,395,113 | B2* | 3/2013 | Grothe, Jr. .................... 250/282 |
| 8,581,176 | B2 | 11/2013 | Thomson et al. |
| 8,686,349 | B2* | 4/2014 | Grothe, Jr. .................... 250/282 |
| 2003/0109990 | A1* | 6/2003 | Axelsson ......................... 702/27 |
| 2003/0229456 | A1* | 12/2003 | Beger et al. ..................... 702/27 |
| 2004/0041091 | A1* | 3/2004 | Bateman et al. ............. 250/282 |
| 2004/0096982 | A1 | 5/2004 | Barnea et al. |
| 2004/0108450 | A1* | 6/2004 | Makarov et al. ............. 250/281 |
| 2005/0067565 | A1 | 3/2005 | Takada et al. |
| 2006/0284068 | A1* | 12/2006 | Amirav et al. ................ 250/282 |
| 2008/0001079 | A1 | 1/2008 | Wang et al. |
| 2008/0208485 | A1 | 8/2008 | Gorenstein et al. |
| 2009/0014639 | A1 | 1/2009 | Bateman |
| 2010/0100336 | A1* | 4/2010 | Wright et al. .................... 702/32 |
| 2010/0213368 | A1 | 8/2010 | Wang et al. |
| 2011/0127419 | A1 | 6/2011 | Thomson et al. |
| 2012/0049056 | A1 | 3/2012 | Zabrouskov et al. |
| 2012/0049058 | A1* | 3/2012 | Grothe, Jr. .................... 250/282 |
| 2012/0108448 | A1* | 5/2012 | Kuhlmann et al. ............... 506/8 |
| 2013/0131998 | A1* | 5/2013 | Wright ............................ 702/27 |
| 2013/0187038 | A1* | 7/2013 | Grothe, Jr. .................... 250/282 |

FOREIGN PATENT DOCUMENTS

| | | |
|---|---|---|
| WO | WO 02/078046 A2 | 10/2002 |
| WO | WO 2005/113830 A2 | 12/2005 |
| WO | WO 2006/130523 A1 | 12/2006 |
| WO | WO 2006/133191 A2 | 12/2006 |
| WO | WO 2007/129107 A2 | 11/2007 |
| WO | WO 2008/003684 A1 | 1/2008 |
| WO | WO 2009/146345 A1 | 12/2009 |

OTHER PUBLICATIONS

S.E. Stein, "An Integrated Method for Spectrum Extraction and Compound Identification from Gas Chromatography/Mass Spectrometry Data," J. Am. Soc. Mass Spectrom., 1999, 10, pp. 770-781.

Biller, et al., "Reconstructed Mass Spectra, a Novel Approach for the Utilization of Gas Chromatography-Mass Spectrometer Data," Analytical Letters (1974), 7(7), 515-28.

Johnstone, et al., "Mass Spectrometry for Chemists and Biochemists," Cambridge University Press, 2nd Edition (1996), pp. 132-134.

Masselon, et al., "Accurate Mass Multiplexed Tandem Mass Spectrometry for High-Throughput Polypeptide Identification from Mixtures," Anal. Chem. 2000, 72, pp. 1918-1924.

Li, et al., "High-Throughput Peptide Identification from Protein Digests Using Data-Dependent Multiplexed Tandem FTICR Mass Spectrometry Coupled with Capillary Liquid Chromatography," Anal. Chem., 2001, 73, pp. 3312-3322.

Wilson, et al., "Multiplexed MS/MS in a Quadrupole Ion Trap Mass Spectrometer," Anal. Chem. 2004, 76, pp. 7346-7353.

Niggeweg, et al., "A general precursor ion-like scanning mode on quadrupole-TOF instruments compatible with chromatographic separation," Proteomics 2006, 6, pp. 41-53.

Venable, et al,, "Cross-Correlation Algorithm for Calculation of Peptide Molecular Weight from Tandem Mass Spectra," Anal. Chem. 2006, 78, pp, 1921-1929.

Geiger, et al., "Proteomics on an Orhitrap Benchtop Mass Spectrometer Using All-ion Fragmentation," Molecular & Cellular Proteomics 9.10 (2010), pp. 2252-2261.

* cited by examiner

*Primary Examiner* — Edward Cosimano

(74) *Attorney, Agent, or Firm* — Thomas F. Cooney

(57) ABSTRACT

A method for matching precursor ions to product ions generated in a chromatography—mass spectrometry experiment comprises: choosing a time window defining a region of interest for precursor ion data and product ion data generated by the experiment; constructing a plurality of extracted ion chromatograms (XICs) for the precursor ion data and the product ion data within the region of interest; automatically detecting and characterizing chromatogram peaks within each XIC and automatically generating synthetic analytical fit peaks thereof; discarding a subset of the synthetic analytical peaks which do not satisfy noise reduction rules; performing a respective cross-correlation score calculation between each pair of synthetic analytical fit peaks; and recognizing matches between precursor ions and product ions based on the cross correlation scores.

19 Claims, 19 Drawing Sheets

METHOD AND APPARATUS FOR CORRELATING PRECURSOR AND PRODUCT IONS IN ALL-IONS FRAGMENTATION EXPERIMENTS

FIELD OF THE INVENTION

This invention relates to methods of analyzing data obtained from instrumental analysis techniques used in analytical chemistry and, in particular, to methods of automatically identifying matches between precursor and product ions, without input from or intervention of a user, in all-ions tandem mass spectral data generated in LC/MS/MS analyses that do not include a precursor ion selection step.

BACKGROUND OF THE INVENTION

Mass spectrometry (MS) is an analytical technique to filter, detect, identify and/or measure compounds by the mass-to-charge ratios of ions formed from the compounds. The quantity of mass-to-charge ratio is commonly denoted by the symbol "m/z" in which "m" is ionic mass in units of Daltons and "z" is ionic charge in units of elementary charge, e. Thus, mass-to-charge ratios are appropriately measured in units of "Da/e". Mass spectrometry techniques generally include (1) ionization of compounds and optional fragmentation of the resulting ions so as to form fragment ions; and (2) detection and analysis of the mass-to-charge ratios of the ions and/or fragment ions and calculation of corresponding ionic masses. The compound may be ionized and detected by any suitable means. A "mass spectrometer" generally includes an ionizer and an ion detector.

One can often enhance the resolution of the MS technique by employing "tandem mass spectrometry" or "MS/MS", for example via use of a triple quadrupole mass spectrometer. In this technique, a first, or parent, or precursor, ion generated from a molecule of interest can be filtered or isolated in an MS instrument, and these precursor ions subsequently fragmented to yield one or more second, or product, or fragment, ions that are then analyzed in a second MS stage. By careful selection of precursor ions, only ions produced by certain analytes are passed to the fragmentation chamber or other reaction cell, such as a collision cell where collision of ions with atoms of an inert gas produces the product ions. Because both the precursor and product ions are produced in a reproducible fashion under a given set of ionization/fragmentation conditions, the MS/MS technique can provide an extremely powerful analytical tool. For example, the combination of precursor ion selection and subsequent fragmentation and analysis can be used to eliminate interfering substances, and can be particularly useful in complex samples, such as biological samples. Selective reaction monitoring (SRM) is one commonly employed tandem mass spectrometry technique.

The hybrid technique of liquid chromatography-mass spectrometry (LC/MS) is an extremely useful technique for detection, identification and (or) quantification of components of mixtures or of analytes within mixtures. This technique generally provides data in the form of a mass chromatogram, in which detected ion intensity (a measure of the number of detected ions) as measured by a mass spectrometer is given as a function of time. In the LC/MS technique, various separated chemical constituents elute from a chromatographic column as a function of time. As these constituents come off the column, they are submitted for mass analysis by a mass spectrometer. The mass spectrometer accordingly generates, in real time, detected relative ion abundance data for ions produced from each eluting analyte, in turn. Thus, such data is inherently three-dimensional, comprising the two independent variables of time and mass (more specifically, a mass-related variable, such as mass-to-charge ratio) and a measured dependent variable relating to ion abundance.

Generally, "liquid chromatography" (LC) means a process of selective retention of one or more components of a fluid solution as the fluid uniformly percolates through a column of a finely divided substance, or through capillary passageways. The retention results from the distribution of the components of the mixture between one or more stationary phases and the bulk fluid, (i.e., mobile phase), as this fluid moves relative to the stationary phase(s). "Liquid chromatography" includes, without limitation, reverse phase liquid chromatography (RPLC), high performance liquid chromatography (HPLC), ultra high performance liquid chromatography (UHPLC), supercritical fluid chromatography (SFC) and ion chromatography.

Generally, the term "HPLC" or "high performance liquid chromatography" refers to liquid chromatography in which the degree of separation is increased by forcing the mobile phase under pressure through a stationary phase, typically a densely packed column. Similarly, the term "UHPLC" or "ultra high performance liquid chromatography" refers to a liquid chromatography technique similar to HPLC except the operating pressures are higher than HPLC (e.g., about 100 MPa vs. about 40 MPa), the columns are typically smaller in diameter, the particles of packing material are generally smaller, and resolution can be greater.

Recent improvements in liquid chromatography (LC) throughput and mass spectrometry (MS) detection capabilities have led to a surge in the use of LC/MS-based techniques for screening, confirmation and quantification of ultra-trace levels of analytes. Currently, the triple quadrupole mass spectrometer is considered the gold standard for quantitation, and SRM techniques are typically used, for example, for the validation of potential biomarkers. Liquid chromatography-triple quadrupole tandem MS (LC/MS/MS) enables highly selective and sensitive quantification and confirmation of hundreds of target compounds in a single run. Unfortunately, such an approach requires extensive compound-dependent parameter optimization and thus requires MS/MS methods to be developed for each analyte. Consequently, the LC/MS/MS approach is restricted to a limited number of compounds per analysis. Moreover, this approach cannot be used to screen for untargeted chemical constituents and does not allow for post acquisition re-interrogation of data.

Because of the above-noted limitations of triple-quadrupole instruments, there is currently a trend towards full-scan MS experiments in residue analysis. Such full-scan approaches utilize high performance time-of-flight (TOF) or electrostatic trap (such as ORBITRAP™-type) mass spectrometers coupled to UHPLC columns and can facilitate rapid and sensitive screening and detection of analytes. The superior resolving power of the ORBITRAP™ mass spectrometer (up to 100,000 FWHM) compared to TOF instruments (10,000-20,000) ensures the high mass accuracy required for complex sample analysis.

An example of a mass spectrometer system 15 comprising an electrostatic trap mass analyzer such as an ORBITRAP™ mass analyzer 25 is shown in FIG. 1. Analyte material 29 is provided to a pulsed or continuous ion source 16 so as to generate ions. Ion source 16 could be a MALDI source, an electrospray source or any other type of ion source. In addition, multiple ion sources may be used. The illustrated system comprises a curved quadrupole trap 18 (also known as a "C-trap") with a slot 31 in the inner electrode 19. Ions are transferred from the ion source 16 to the curved quadrupole trap 18 by ion optics assembly 17 (e.g. an RF multipole). Prior to ion injection, ions may be squeezed along the axis of the curved quadrupole trap 18 by raising voltages on end electrodes 20 and 21. For ion injection into the ORBITRAP™ mass analyzer 25, the RF voltage on the curved quadrupole trap 18 may be switched off, as is well known. Pulses are applied to electrodes 19 and 22 and to an electrode of curved ion optics 28 so that the transverse electric field accelerates ions into the curved ion optics 28. The converging ion beam that results enters the ORBITRAP™ mass analyzer 25 through injection slot 26. The ion beam is squeezed towards the axis by an increasing voltage on a central electrode 27. Due to temporal and spatial focusing at the injection slot 26, ions start coherent axial oscillations. These oscillations produce image currents that are amplified and processed. Further details of the electrostatic trap apparatus 25 are described in International Application Publication WO 02/078046, U.S. Pat. No. 5,886,346, U.S. Pat. No. 6,872,938. The ion optics assembly 17, curved quadrupole trap 18 and associated ion optics are enclosed in a housing 30 which is evacuated in operation of the system.

The system 15 (FIG. 1) further comprises reaction cell 23, which may comprise a collision cell (such as an octopole) that is enclosed in a gas tight shroud 24 and that is aligned to the curved quadrupole trap 18. The reaction cell 23, when used as a collision cell, may be supplied with an RF voltage of which the DC offset can be varied. A collision gas line (not shown) may be attached and the cell is pressurized with nitrogen (or any) gas.

Higher energy collisions (HCD) may take place in the system 15 as follows: Ions are transferred to the curved quadrupole trap 18. The curved quadrupole trap is held at ground potential. For HCD, ions are emitted from the curved quadrupole trap 18 to the octopole of the reaction cell 23 by setting a voltage on a trap lens. Ions collide with the gas in the reaction cell 23 at an experimentally variable energy which may be represented as a relative energy depending on the ion mass, charge, and also the nature of the collision gas (i.e., a normalized collision energy). Thereafter, the product ions are transferred from the reaction cell back to the curved quadrupole trap by raising the potential of the octopole. A short time delay (for instance 30 ms) is used to ensure that all of the ions are transferred. In the final step, ions are ejected from the curved quadrupole trap 18 into the ORBITRAP™ mass analyzer 25 as described previously.

The mass spectrometer system 15 illustrated in FIG. 1 lacks a mass filtering step and, instead, causes fragmentation of all precursor ions at once, without first selecting particular precursor ions to fragment. Accordingly, the equivalent of a tandem mass spectrometry experiment is performed as follows: (a) a first sample of ions (comprising a plurality of types of ions) produced from an eluting chemical compound are transferred to and captured by the curved quadrupole trap 18; (b) the first sample of ions is transferred to the ORBITRAP™ mass analyzer 25 as described above for analysis, thereby producing a "full-scan" of the ions; (c) after the first sample of ions has been emptied from the curved quadrupole trap 18, a second sample of ions from the same chemical compound are transferred through the curved quadrupole trap 18 to the reaction cell 23; (d) in the reaction cell, a plurality of different types of fragment ions are formed from each of the plurality of ion types of the second sample of the chemical compound; (e) once the ORBITRAP™ mass analyzer 25 has been purged of the first sample of ions, the fragment ions are transferred back quadrupole trap 18 and then to the ORBITRAP™ mass analyzer 25 for analysis as described above. Such "all-ions-fragmentation scanning" provides a potential multiplexing advantage, but only if the analysis firmware or software can successfully extract precursor-product relationships between the thousands of ions generated in the all-ions-fragmentation scan and the additional thousands of ions present in the full-MS precursor scan.

An early approach to simplifying the above problem of many overlapping ion signals was developed by Biller and Biemann (Anal Letters, July 1974) who realized that significant improvement in component detection relative to a Total Ion Current (TIC) chromatogram can be achieved by constructing synthetic chromatograms that only include those ion masses that maximize at a given time. In the Biller and Biemann technique, the data is analyzed at each value of m/z. Each such value of m/z gives rise to an extracted ion chromatogram (XIC) which conveys information about the time-variation of detected intensities of ions having only the particular respective m/z under consideration. When the intensities of several ions in respective extracted ion chromatograms simultaneously rise to a maximum, thereby forming a peak, the Biller and Biemann technique considers that a chromatographic peak has been detected. Such chromatic peak is constructed as the summation of intensities of the ions that form peaks, ignoring other ions that do not form peaks at the same time. Such reconstructed chromatograms can be used with success to conduct searches against a database of compounds (Gray and Abel, U.S. Pat. No. 5,453,613).

Unfortunately, a deficiency of the Biller and Biemann technique is that a maximum in an ion intensity is not a guarantee that a compound eluted at that time. Johnstone and Rose (Johnstone and Malcolm E. Rose, "Mass Spectrometry for chemists and biochemists", 2nd Edition, Cambridge University Press (1996), pp. 132-134) further noted that, employing the Biller and Biemann technique, " . . . deconvolution of the mass spectra of co-eluting components cannot be effected because all component ions will maximize in the same scan." In general, attempting to characterize a chromatographic peak with a maximum value only does not capture all the information available from better and more-recently-developed methods of peak detection. One such method is the technique of Parameterless Peak Detection (PPD) which is described in United States Patent Application publication 2010/0100336 A1 titled "Methods of Automated Spectral Peak Detection and Quantification without User Input" and assigned to the assignee of the present invention. By using PPD, potential chromatographic peaks are rigorously examined and spurious ones eliminated, and multiple quality parameters are available on those peaks which pass, to allow further characterization of these peaks. Accordingly, from the foregoing discussion, there is a need in the art for reproducible methods of automated detection, location and area calculation of peaks that do not require initial parameter input or other intervention by a user or operator. The present invention addresses such a need.

SUMMARY

The inventor of the present invention has realized that the technique of Parameterless Peak Detection (PPD) is useful to match precursor and product ions that experienced the same chromatographic response and have similar lineshapes. Embodiments in accordance with the present teachings may address the above-noted needs in the art by providing methods employing a stepwise approach. In one step, peaks are automatically detected by the methods of parameterless peak detection (PPD) and located within each of a plurality of extracted ion chromatograms (XICs) derived from time-based mass spectrometry data obtained during LC/MS analysis. During this process, peak information is retained only for those ions for which chromatographic peaks occur. Further, as peaks are detected, they are subjected to a few quality tests that are unique to XIC data. Since the extracted ion chromatograms should not be complex chromatograms with many overlapping peaks, the first rule is that the area of a peak must be an appreciable fraction of the area remaining in the XIC. Also, while the PPD technique can do an excellent job of extracting peak shapes from large "lumpy" regions, such features are not to be expected in extracted ion chromatograms, and, therefore, an additional test is employed such that each peak intensity must large with respect to the average intensity. These constraints are particularly effective in reducing "noise" when employed with XIC data. Accordingly, this step provides a significant data size reduction. The result or output of this step is either a filtered data file written to computer-readable media, or a list of components found in the original data, or both. The automatic peak detection and location techniques do not make a priori assumptions about the particular line shape of the chromatographic or spectroscopic peak(s) and may fit any individual peak to either a Gaussian, exponentially modified Gaussian, Gamma distribution or to another form or to a composite form comprising more than one of the above peak forms.

In a subsequent step, the remaining ions are grouped by calculating the cross correlations of relevant parameters pairwise between the various remaining peaks. To perform this calculation, a vector is constructed for each peak, and a correlation coefficient is computed between each vector and every other vector. In some embodiments, each vector may consist of 11 variables: the mass defect, the width, and 9 intensity values obtained from the parametric determination of peak shape. The time points of the intensity values cover the region of the XIC where PPD has determined that a peak exists.

It has been found that execution of just the steps described above is very effective and often leads to correct synthetic MS/MS spectra without the necessity of additional analysis, or, perhaps, just a simple final pruning of the computed MS/MS spectrum from first principles of High Mass Accuracy ion detection (e.g., whether there exists a plausible chemical formula that matches an observed mass difference within instrumental precision). If necessary, a final step may be performed in which remaining ambiguities in the matches between precursor and product ions are resolved based on putative fragmentation pathways and chemical composition. That is, m/z values that, after converting to mass by determining charge state, gain credibility if they correspond to plausible chemical formulae. And, since mass spectrometers such as those described herein typically have better precision than accuracy, the criterion used is that the neutral loss mass should correspond to a formula, not the precursor or product masses. After mass calibration, of course, all masses should be identified with a formula (or list of formulae), but the calibration step is not necessary when only the neutral loss mass is used.

Since there are typically only 1,000 to 10,000 components in a data file, this calculation is rapid, and the resulting correlation score can be used to eliminate ions that are not closely related to the ion under consideration. Typically only 5-20 masses are highly correlated, and this makes the construction of fragmentation pathways entirely practical.

According to first aspect of the invention, there is provided a method for matching precursor ions to product ions generated in a chromatography—mass spectrometry experiment comprising: choosing a time window defining a region of interest for precursor ion data and product ion data generated by the experiment; constructing a plurality of extracted ion chromatograms (XICs) for the precursor ion data and the product ion data within the region of interest; automatically detecting and characterizing chromatogram peaks within each XIC and automatically generating synthetic analytical fit peaks thereof; discarding a subset of the synthetic analytical peaks which do not satisfy noise reduction rules; performing a respective cross-correlation score calculation between each pair of synthetic analytical fit peaks; and recognizing matches between precursor ions and product ions based on the cross correlation scores.

According to a second aspect of the invention, there is provided an apparatus comprising: (a) a chromatograph for providing a stream of separated chemical substances; (b) a mass spectrometer fluidically coupled to the chromatograph for generating a plurality of precursor ions and a plurality of product ions resulting from simultaneous fragmentation of each of the precursor ions; (c) a detector for detecting abundance data for each product ion and each product ion; and (d) a programmable electronic processor electrically coupled to the mass spectrometer, the programmable processor comprising instructions operable to cause the programmable processor to: (i) receive the abundance data for each of the product ions and precursor ions; (ii) automatically detect and characterize chromatogram peaks as a function of time for each of a plurality of mass-to-charge ratio ranges of the abundance data for the product ions and precursor ions; (iii) automatically generate synthetic analytical fit peaks to the detected chromatogram peaks; (iv) automatically discard a subset of the synthetic analytical fit peaks which do not satisfy noise reduction rules; (v) automatically perform a respective cross-correlation score calculation between each pair of synthetic analytical fit peaks; and (vi) automatically recognize matches between precursor ions and product ions based on the cross correlation scores.

BRIEF DESCRIPTION OF THE DRAWINGS

The above noted and various other aspects of the present invention will become apparent from the following description which is given by way of example only and with reference to the accompanying drawings, not drawn to scale, in which.

DETAILED DESCRIPTION

The present invention provides methods and apparatus for correlating precursor and product ions in all-ions fragmentation experiments (or experiments including other types of ion reactions that yield product ions). The automated methods and apparatus described herein do not require any user input or intervention. The following description is presented to enable any person skilled in the art to make and use the invention, and is provided in the context of a particular application and its requirements. Various modifications to the described embodiments will be readily apparent to those skilled in the art and the generic principles herein may be applied to other embodiments. Thus, the present invention is not intended to be limited to the embodiments and examples shown but is to be accorded the widest possible scope in accordance with the features and principles shown and described. The particular features and advantages of the invention will become more apparent with reference to the appended FIGS. 2, 3, 4A, 4B, 5, 6, 7, 8, 9, 10A, 10B, 10C, 11, 12, 13, 14A, 14B, 15A, 15B, 15C, 16 and 17, taken in conjunction with the following description.

Section 1. General Considerations

Figure 1:
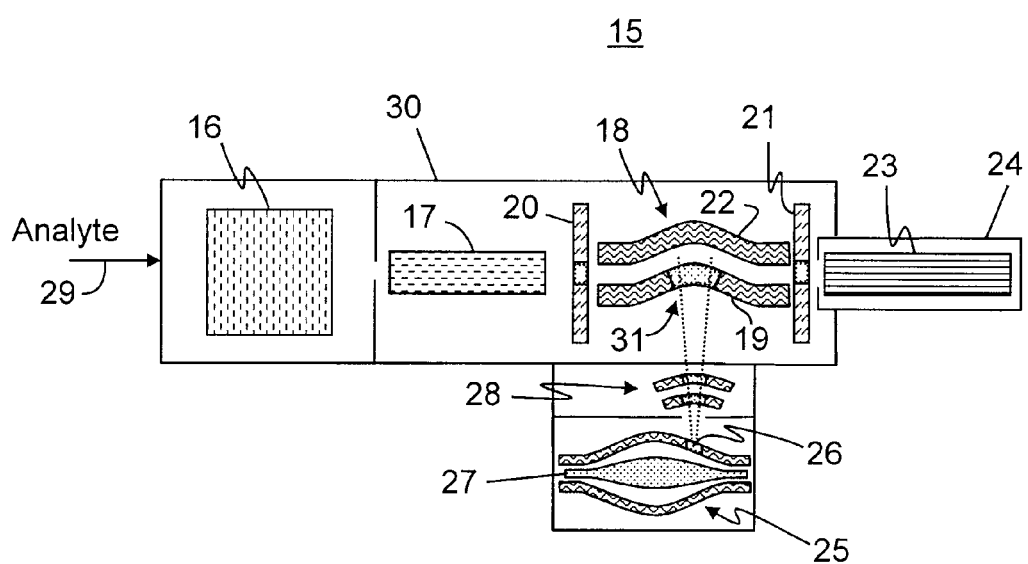
FIG. 1 is a schematic illustration of an example of a mass spectrometer system comprising an electrostatic trap mass analyzer such as an ORBITRAP™ mass analyzer.
Figure 2:
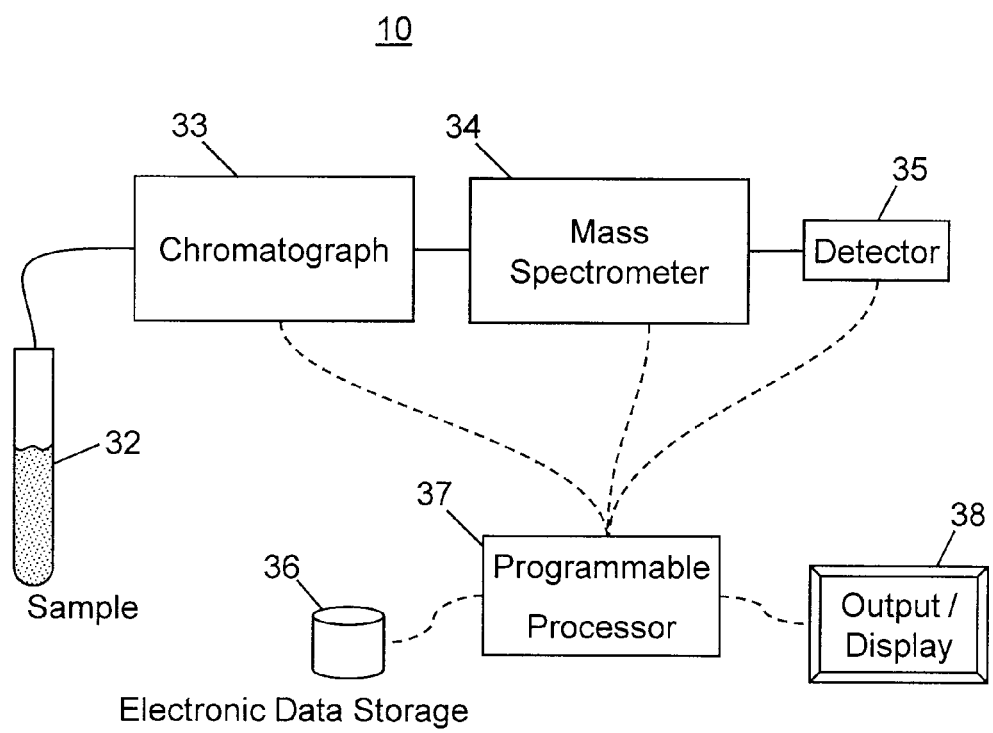
FIG. 2 is a schematic diagram of a system for generating and automatically analyzing chromatography/mass spectrometry spectra in accordance with the present teachings.

FIG. 2 is a schematic diagram of a system 10 for generating and automatically analyzing chromatography/mass spectrometry spectra in accordance with the present teachings. A chromatograph 33, such as a liquid chromatograph, high-performance liquid chromatograph or ultra high performance liquid chromatograph receives a sample 32 of an analyte mixture and at least partially separates the analyte mixture into individual chemical components, in accordance with well-known chromatographic principles. As a result, the at least partially separated chemical components are transferred to a mass spectrometer 34 at different respective times for mass analysis. As each chemical component is received by the mass spectrometer, it is ionized by an ionization source of the mass spectrometer. The ionization source may produce a plurality of ions (i.e., a plurality of precursor ions) comprising differing charges or masses from each chemical component. Thus, a plurality of ions of differing mass-to-charge ratios may be produced for each chemical component, each such component eluting from the chromatograph at its own characteristic time. These various ions are analyzed and detected by the mass spectrometer together with its detector 35 and, as a result, appropriately identified according to their various mass-to-charge ratios. As illustrated in FIG. 1, the mass spectrometer comprises a reaction cell to fragment or cause other reactions of the precursor ions but may lack a mass filtering step for selection of particular ions to introduce into the reaction cell. In such a situation, the reaction cell, instead, causes reactions to or fragmentation of all ions at once.

Still referring to FIG. 2, a programmable processor 37 of the system 10 is electronically coupled to the detector of the mass spectrometer and receives the data produced by the detector during chromatographic/mass spectrometric analysis of the sample(s). The programmable processor may comprise a separate stand-alone computer or may simply comprise a circuit board or any other programmable logic device operated by either firmware or software. Optionally, the programmable processor may also be electronically coupled to the chromatograph and/or the mass spectrometer in order to transmit electronic control signals to one or the other of these instruments so as to control their operation. The nature of such control signals may possibly be determined in response to the data transmitted from the detector to the programmable processor or to the analysis of that data. The programmable processor may also be electronically coupled to a display or other output 38, for direct output of data or data analysis results to a user, or to electronic data storage 36.

The programmable processor of the system 10 shown in FIG. 2 is generally operable to: receive a precursor ion chromatography/mass spectrometry spectrum and a product ion chromatography/mass spectrometry spectrum from the chromatography/mass spectrometry apparatus; generate and evaluate a plurality of extracted ion chromatograms (XICs) of each of the precursor ion and product ion spectra; automatically subtract a baseline from each such XIC so as to generate a plurality of baseline-corrected XICs; automatically detect and characterize all spectral peaks occurring above a noise level in each baseline-corrected XIC; perform a cross-correlation calculation between each pair of detected peaks; and report or record information relating to the peaks, to the cross-correlations between the peaks or to possible product-precursor matches derived from the cross-correlation calculations.

Figure 3:
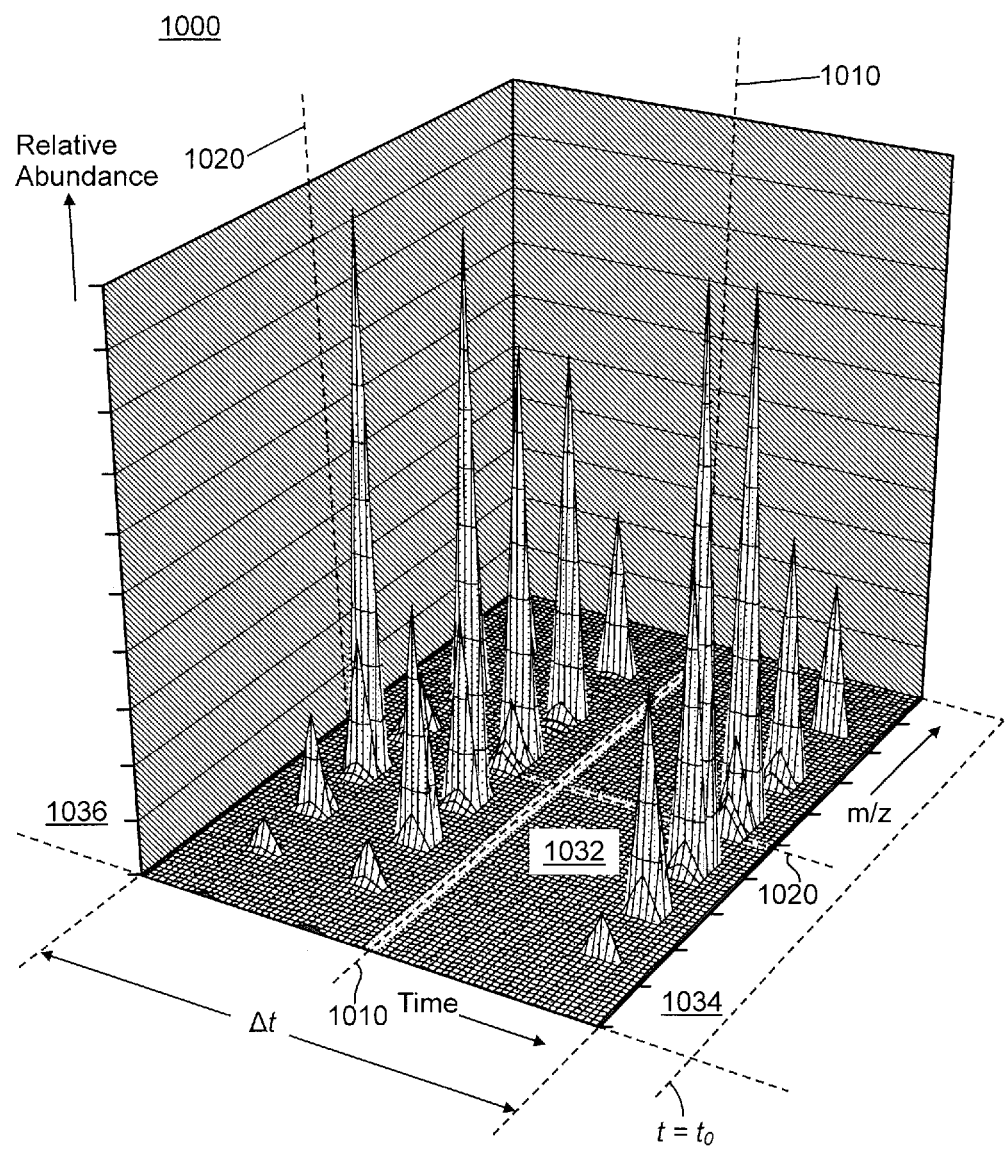
FIG. 3 is a perspective view of a three-dimensional graph of chromatography-mass spectrometry data, in which the variables are time, mass (or mass-to-charge ratio, m/z) and ion abundance.

FIG. 3 is a perspective view of a three-dimensional graph 1000 of hypothetical LC/MS data. As is common in the representation of such data, the variables time and mass (or mass-to-charge ratio, m/z) are depicted on the "floor" of the perspective diagram and the variable representing ion abundance (for instance, detected ion current) is plotted in the "vertical" dimension of the graph. Thus, ion abundance is represented as a function of the other two variables, this function comprising a variably shaped surface above the "floor". Each set of peaks dispersed and in line parallel to the m/z axis represents the various ions produced by the ionization of a single eluting analyte (or, possibly, of fortuitously co-eluting analytes) at a restricted range of time. In a well-designed chromatographic experiment, each analyte of a mixture will elute from the column (thereby to be mass analyzed) within a particular diagnostic time range. Consequently, either a single peak or a line of mass-separated peaks, each such peak representing a particular ion produced by the eluting analyte, is expected at each elution time (or retention time) range.

For clarity, only a very small number of peaks are illustrated in graph 1000 of FIG. 3. In practice, data obtained by a chromatography-mass spectrometry experiment may comprise a very large volume of data. A mass spectrometer may generate a complete "scan" over an entire mass range of interest in a matter of tens to hundreds of milliseconds. As a result, up to several hundred complete mass spectra may be generated every second. Further, the various analytes may elute over a time range of several minutes to several tens of minutes, depending on the complexity of the mixture under analysis and the range of retention times represented.

When the chromatography-mass spectrometry experiment and data generation are performed by a mass spectrometer system that performs both all-ion precursor ion scanning and all-ions product ion scanning, the data for each eluent will logically comprise two data subsets, each of which is similar to the data set illustrated in graph 1000 of FIG. 3. One of these data subsets will contain the data for the precursor ions and the other data subset will contain the data for the product ions. Such a situation is illustrated schematically in FIGS. 15A, 15B and 15C, discussed in greater detail in following paragraphs. Generally, the data set containing the product ion peaks will also contain some peaks corresponding to residual un-fragmented or un-reacted precursor ions.

Returning to the discussion of FIG. 3, the data depicted in graph 1000 therein may comprise an entire stored data file representing results of a prior experiment. Alternatively, the data represent a portion of a larger data set in the process of being acquired by an LC/MS instrument. For instance, the data depicted in graph 1000 of FIG. 3 may comprise recently collected data held in temporary computer readable memory, such as a memory buffer, and corresponding to an analysis time window, $\Delta t$, upon which calculations are being formed while, at the same time, newer data is being collected. Such newer, not-yet-analyzed data is represented, in time and m/z space, by region 1034 and the data actually being collected is represented by the line $t=t_0$. Older data which has already been analyzed by methods of the present teachings and which has possibly been stored to a permanent computer readable medium, is represented by region 1036. With such manner of operation, methods in accordance with the present teachings are carried out in near-real-time on an apparatus used to collect the data or using a processor (such as a computer processor) closely linked to the apparatus used to collect the data.

Figure 15A:
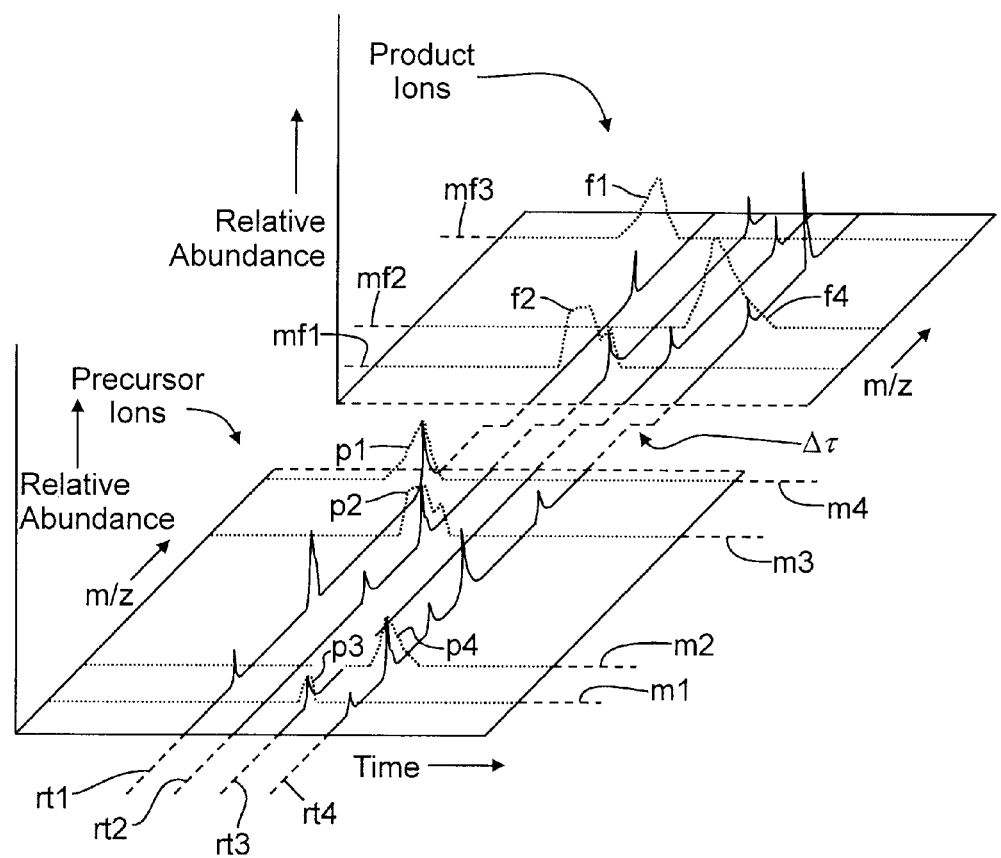
FIG. 15A is a perspective view of a three-dimensional graph of chromatography-mass spectrometry data showing four hypothetical mass spectra of precursor ions and corresponding mass spectra of product ions and showing hypothetical extracted ion chromatograms (XICs) for several different values of mass-to-charge ratio.

Operationally, data such as that illustrated in graph 1000 of FIG. 3 is collected as separate mass spectra (also referred to herein as "scans"), each mass spectrum (scan) corresponding to a particular respective time point. Such mass spectra may be envisioned as residing within planes parallel to the plane indicated by the trace lines 1010 in graph 1000 of FIG. 3 or parallel to the lines rt1, rt2, rt3 and rt4 in FIG. 15A. As illustrated in FIG. 15A, each precursor-ion scan corresponds to a respective product-ion scan. Once at least a portion of data has been collected, such as the data in region 1032 in graph 1000 of FIG. 3, then the information, in the data portion may be logically re-organized as extracted ion chromatograms (or, at least portions thereof). Each such XIC may be envisioned as a cross section through the data in a plane parallel to the plane indicated by trace lines 1020 in graph 1000 of FIG. 3 or parallel to the lines m1, m2, m3, m4, mf1, mf2, and mf3 in FIG. 15A. Hypothetical extracted ion chromatograms are shown as dotted lines in FIG. 15A and FIG. 15B. Each XIC represents the elution profile, in time, of ions of a particular mass-to-charge range. The XIC representation of the data is useful for understanding the methods of the present teachings.

Figure 15B:
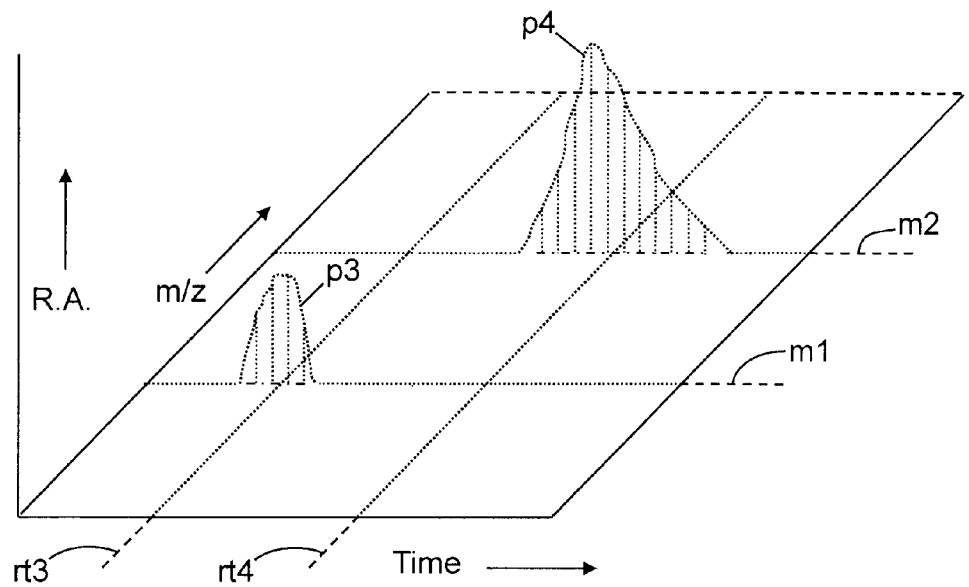
FIG. 15B is a perspective view of a portion of the three-dimensional graph of FIG. 15A showing selected peaks as extracted ion chromatograms.
Figure 15C:
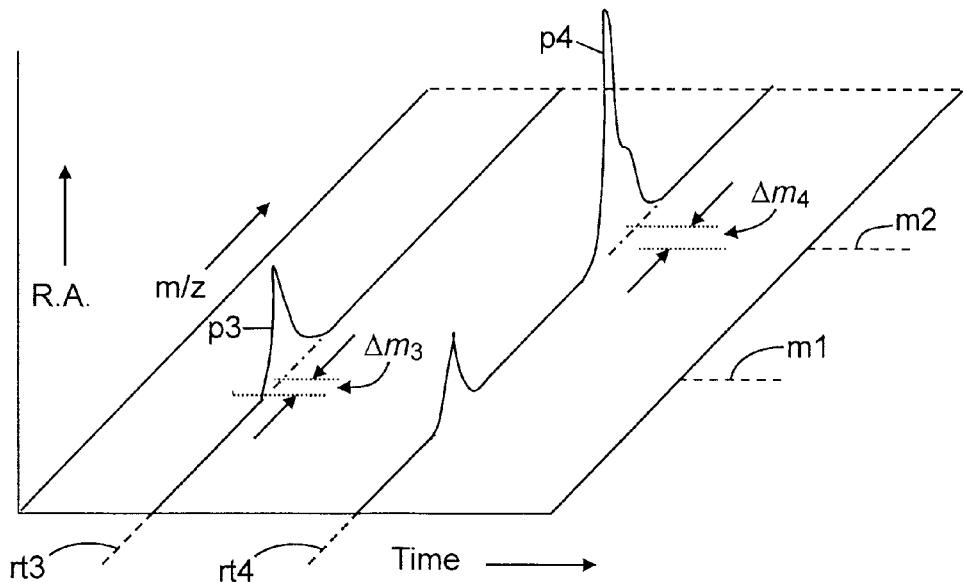
FIG. 15C is a perspective view of a portion of the three-dimensional graph of FIG. 15A showing selected peaks as mass scans.

Several schematic hypothetical XIC profiles are shown in FIGS. 15A, 15B and 15C. These profiles include several example peaks. The illustrated precursor scan peaks are peak p1 at coordinates (rt1, m4), peak p2 at coordinates (rt2, m3), peak p3 at coordinates (rt3, m1) and peak p4 at coordinates (rt4, m2). Three product ion scan peaks are also illustrated: peak f1 at coordinates (rt1, mf3), peak f2 at coordinates (rt2, mf1) and peak f4 at coordinates (rt4, mf2). As described above with respect to the operation of the spectrometer system 15 (FIG. 1), the precursor-ion and product-ion scans alternate in time. Thus, even though the time lines rt1, rt2, rt3 and rt4 correspond to the maximum production of precursor ions of different nearly-co-eluting compounds, the respective immediately following product ion scans are offset in time, relative to the maxima, by a time delay increment $\Delta \tau$. The system 15 illustrated in FIG. 1 is capable of repeating the precursor scan and product ion scan sequence five times for compounds that elute over a period of 1 second (that is, 10 total scans per second). Thus, even though precursor ion and product ion scans are not coincident in time, there are generally a sufficient number of precursor ion scans and product ion scans to permit discernment of the profiles of the peaks.

1.1. High-Level Methods

Figure 4A:
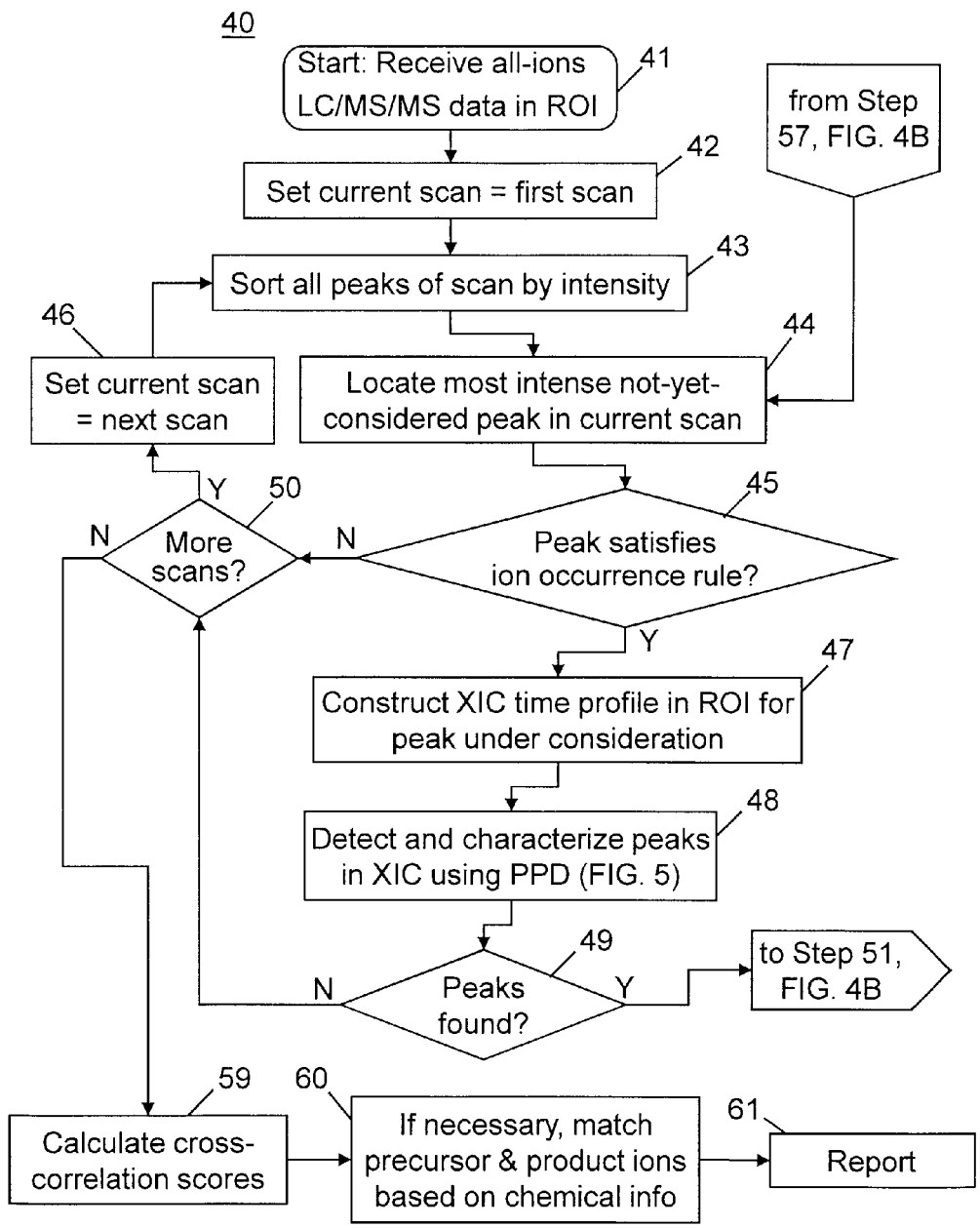
FIGS. 4A-4B provide a flowchart of a method for generating automated correlations between all-ions precursor ions and all-ions-fragmentation product ions in accordance with the present teachings.
Figure 4B:
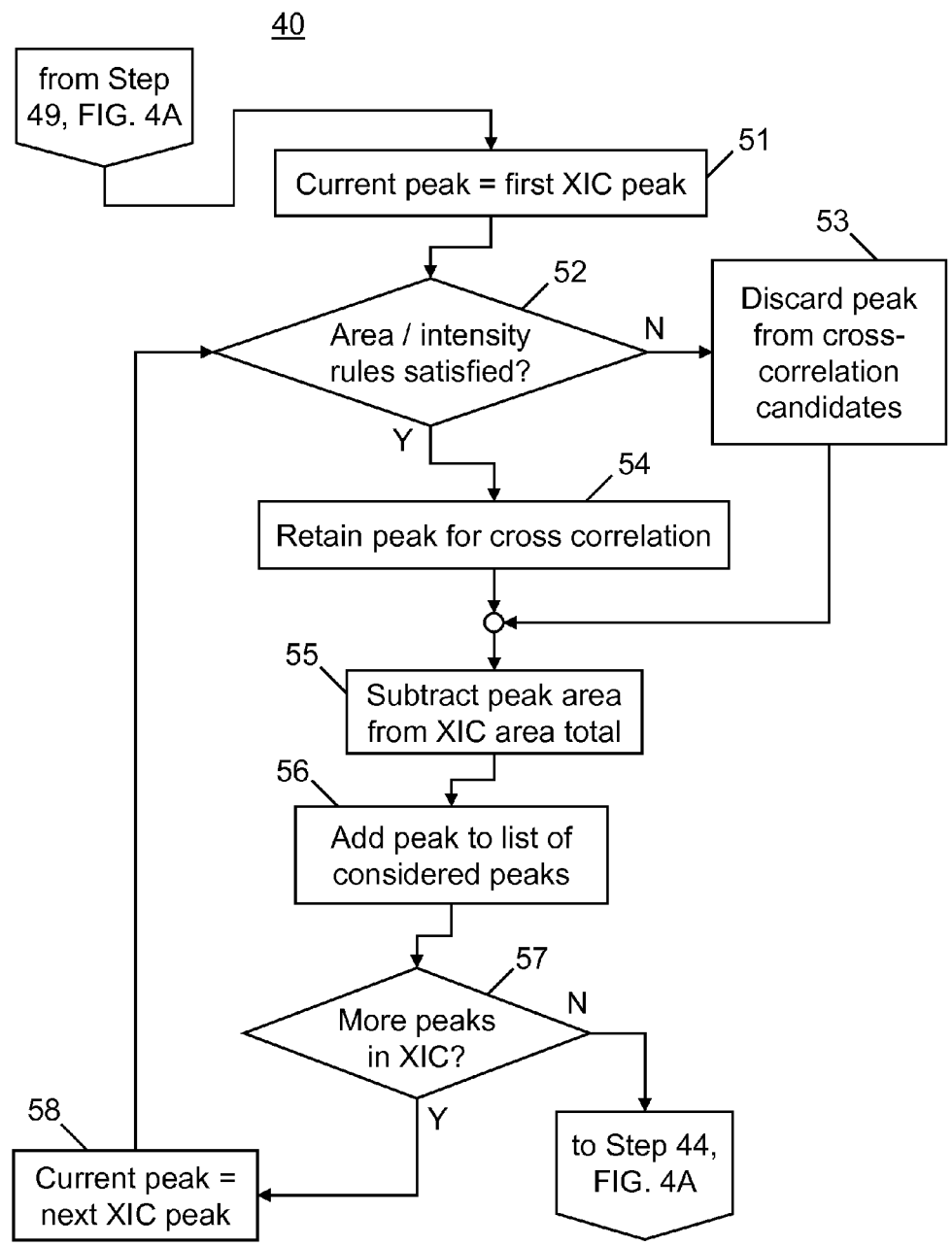

FIGS. 4A-4B present a flowchart of a method 40 for generating automated correlations between all-ions precursor ions and all-ions-fragmentation product ions in accordance with the present teachings. In the initial step, step 41 (FIG. 4A), all-ions LC/MS/MS data is generated by and received from a chromatograph-mass spectrometer apparatus. The LC/MS data comprises two data subsets, as shown in FIG. 15A—one data subset containing data for precursor ions and the other data subset containing data for all the product ions formed by reaction or fragmentation of all the precursor ions. Each data subset comprises ion abundance (or relative abundance) information as a function of time and m/z.

The calculations of method 40 are performed on a chosen time window of the data set. This time-window corresponds to a current region of interest (ROI) of recently collected data, such as region 1032 of graph 1000 of FIG. 3. The region of interest includes data (e.g., see FIG. 15A) from the precursor ion scan (MS scan) as well as the product ion scan (MS/MS scan). In embodiments, this window is 1.4 minutes wide, but other window widths will work equally well as long as the window width is greater than the expected peak width. Good results have been obtained by the inventor using window widths of 0.5 minutes and 0.2 minutes. These time windows represent a small portion of a typical chromatographic experiment which may run for several tens of minutes to on the order of an hour. For data dependent instrument control, a much smaller time window would probably be used. Such data dependent instrument control functions may be performed in automated fashion, wherein the results obtained by the methods herein are used to automatically control operation of the instrument at a subsequent time during the same experiment from which the data were collected. For instance, based on the results of the algorithms, a voltage may be automatically adjusted in an ion source or a collision energy (that is applied to ions in order to cause fragmentation) may be adjusted with regard to collision cell operation. Such automatic instrument adjustments may be performed, for instance, so as to optimize the type or number of ions or ion fragments produced.

At a high- or most-general level, any algorithm that systematically examines the data of the region of interest in the time window, searching for peaks to be tested by subsequent cross-correlation calculation, may be employed. For example, an algorithm may march through the data, scan-by-scan, and in two parallel processes, one for each scan type. In the present example, the window width is only 0.7 minutes wide at time zero since there is no data before time=0. As scans of higher time are examined, the window increases until the scan at time 0.7 minutes uses a window of the specified 1.4 minutes.

In step 42 of the present example (FIG. 4A), the scan to be examined (the current scan) is set to be the initial scan within the ROI. This is an initialization step for a loop in which scans are sequentially examined. In step 43, the peaks of the current scan are sorted by intensity and the ions are examined one by one, starting with the most intense (step 44). In general, all ions are examined, but for very rapid work or strong signals, a threshold may be applied and only ions with intensities above threshold examined. In the present example, step 59 (described in greater detail later in this document) is performed when all ions in all scans of the ROI have been examined. In Step 45 of this example, the occurrence of an ion is noted, and its history or time-profile is compared to a rule for ions to be considered as forming a peak. A preferred rule that is used is that the ion must occur in three contiguous scans (scans of the same type), but any rule based on ion appearance and scan number may be used. For example, a rule that the ion must appear in 3 of 5 contiguous scans might alternatively be chosen. (Ions are considered identical if they agree within the mass tolerance, and as an ion history is accumulated, any new occurrence is compared to the average value of the previous instances, not simply the previous instance.)

If, in step 45, the peak does not satisfy the ion occurrence rule, then, if there are more unexamined scans in the ROI (determined in step 50), the current scan is set to be the next unexamined scan (step 46) and the method returns to step 43 to begin examining the new current scan. If the ion occurrence rule (as determined in step 45) is satisfied, then an extracted ion chromatogram corresponding to the m/z range of the ion peak under consideration is constructed in step 47. It is to be noted that the terms "mass" and "mass-to-charge" ratio, as used here, actually represent a small finite range of mass-to-charge ratios. The width or "window" of the mass-to-charge range is the stated precision of the mass spectrometer instrument. The technique of Parameterless Peak Detection (PPD, see FIG. 5 and discussion thereof as well as United States Patent Application publication 2010/0100336 A1) then attempts to find peaks in an extracted ion chromatogram (XIC) corresponding to this 1.4 minute time window in step 48. Once this particular mass has been tested for peaks in the XIC, it is not tested again until the center of the time window has increased by the window size. (So, for example, if an ion is tested for peaks when the time window is 2-3.4, it will not be tested again until the window is 3.4-4.8.)

Subsequent steps of the method 40 are performed using the analytical functions provided by the synthetic fitted peaks generated by PPD (or calculated peak parameters) instead of using the original data. If, in the decision step 49, no peaks are found by PPD for the mass under consideration, then, if there are remaining unexamined scans (step 50), the method returns back to step 46 and then step 43. However, if peaks are found, then the method continues to step 51 (FIG. 4B) in which the first of possibly several peaks in the XIC is set for initial consideration. In the next step 52, for each peak found by PPD, additional rules of large relative area and high relative intensity (described in further detail in the next paragraph) are applied. Peaks that fail these tests are discarded (step 53), whereas those that pass are accepted and retained (step 54) for further processing by cross-correlation score calculations (such correlation scores are calculated in step 59). Regardless of whether or not a peak is accepted, after each peak is considered, the peak area of the peak is subtracted (step 55) from the total area used in the relative area criterion in subsequent iterations of step 52. Also (step 56) the peak is added to a list of peaks within the ROI that have been examined, to prevent possible duplicate consideration of a single peak.

The step 52 of the method 40 is now discussed in more detail. In step 52, the area of, $A_j$, of the peak currently under consideration (the $j^{th}$ peak) is noted. Also, the total area ($\Sigma A$) under the curve the fitted chromatogram and the average peak height ($I_{ave}$) of any remaining peaks in the fitted chromatogram are calculated. The area $\Sigma A$ is the area of the data remaining after any previous peaks have been detected and removed. The step 52 compares the area, $A_j$, of the most recently found peak to the total area ($\Sigma A$). Also, this step compares the peak maximum intensity, $I_j$, of the most recently found peak is compared to $I_{ave}$. If it is found either that $(A_j/\Sigma A)<\omega$ or that $(I_j/I_{ave})<\rho$, where $\omega$ and $\rho$ are pre-determined constants, then the execution of the method 40 branches to step 53 in which the peak is removed from a list of peaks to be considered in—and is thus eliminated from consideration in—the subsequent cross-correlation score calculation step.

Figure 10A:
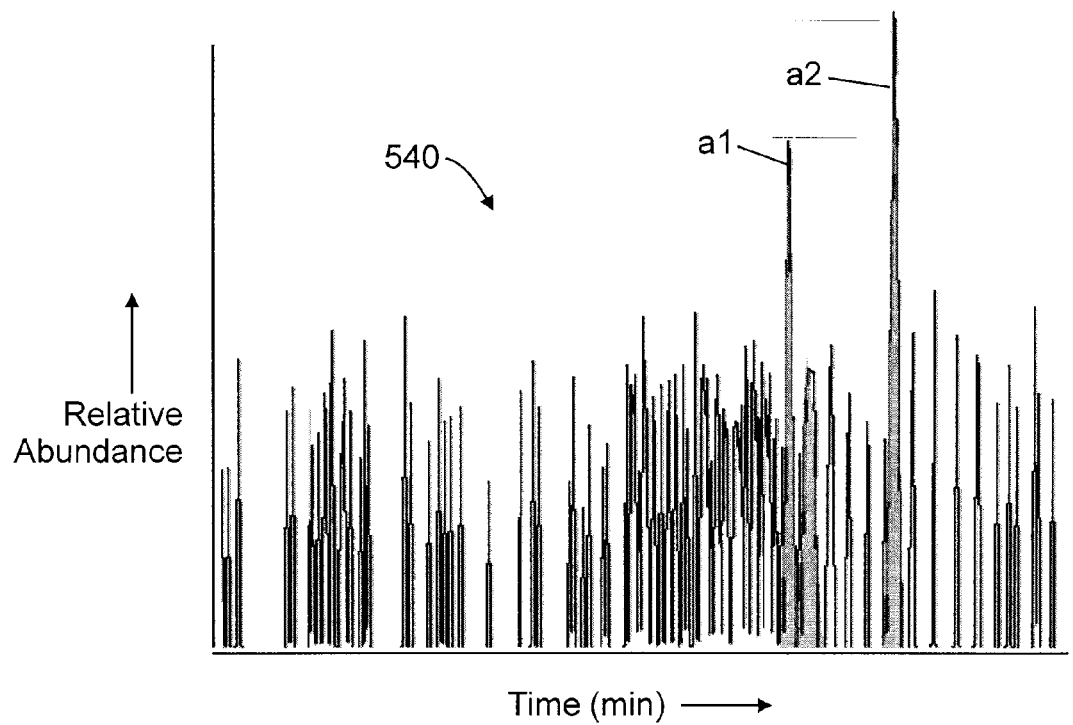
FIGS. 10A, 10B and 10C are graphical examples of discrimination of peaks of interest from noise peaks in an ion chromatogram.
Figure 10B:
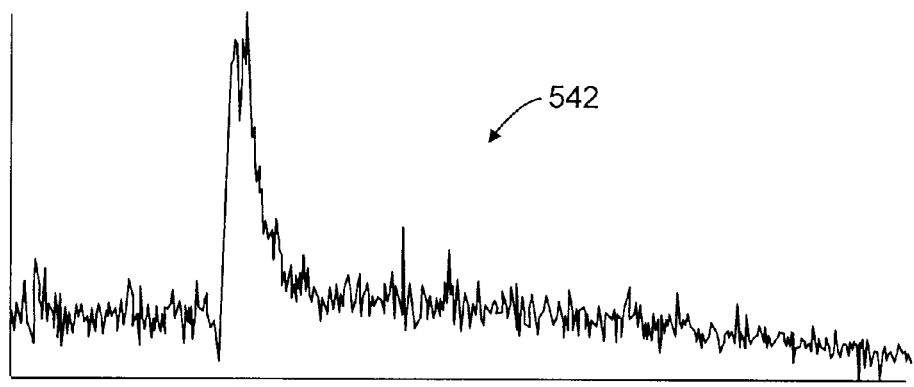
Figure 10C:
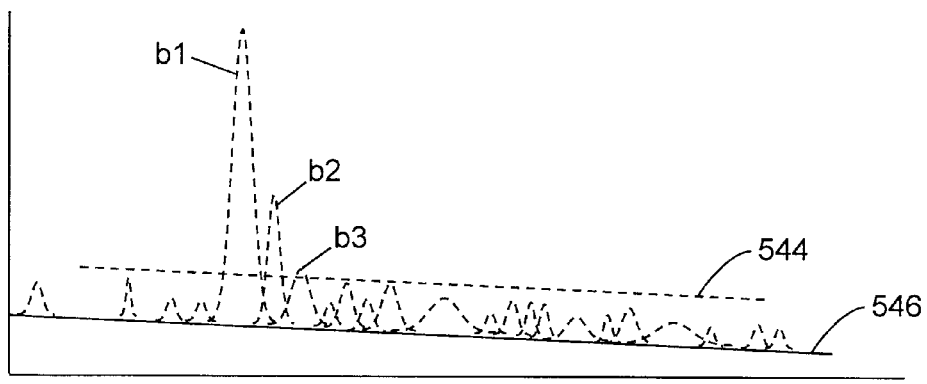

The removal of certain peaks in this fashion renders the fitted peak set consistent with the expectations that, within an XIC, each actual peak of interest should comprise a significant peak area, relative to the total peak area and should comprise a vertex intensity that is significantly greater than the local average intensity. FIGS. 10A, 10B and 10C schematically illustrate this concept. For instance, after peak discrimination in step 52 (FIG. 4B), fitted peaks corresponding to data peaks a1 and a2 in of the XIC 540 in FIG. 10A may, in some embodiments, not be retained in the list of peaks to be tested by cross correlation as a result of their relatively smaller peak areas in relation to the total area above the baseline. In various embodiments, the retention of peaks may be determined based on statistical considerations—such as correlation statistics between different data files—or possibly some other criteria related to relative peak areas. Numerous fitted peaks in FIG. 10C, which represent a fit to the XIC 542 of FIG. 10B, are eliminated by a different criterion. For example, all fitted peaks in FIG. 10C that do not extend above line 544 may be eliminated because their peak heights do not meet a peak height criterion, even though the areas of several of them are not insignificant. In the illustrated example, line 546 is a baseline and line 544 is a line offset from the baseline such that the vertical distance between the two lines represents a minimum peak height for acceptance. Thus, in this case, only peaks b1, b2 and b3 are retained. In various embodiments, the retention of peaks may be determined based on statistical considerations or some other criteria related to relative peak heights.

Returning to the discussion of the method 40 (FIG. 4B), it may be noted that if the decision step 57 determines that more peaks exist in the XIC under consideration, then the method branches to step 58 in which the next peak is set for consideration and then back to step 52. If, however, it is determined that no additional peaks remain the XIC, then execution goes back to step 44 (FIG. 4A) so as to continue examining additional peaks (if any) in the current scan. The above-described sequence continues until all peaks in all scans have been examined and, consequently, all peaks to be used for matching have been identified. Subsequently, in Step 59, the cross correlation for each retained XIC peak is calculated with respect to every other mass that formed an XIC peak in the region of interest. Each detected precursor peak is considered, through a cross-correlation calculation, against each detected product ion peak in order to match precursor ions with product ions. The details of the calculations are presented in a subsequent section herein.

In the optional step, step 60, any remaining ambiguities in the matches between precursor and product ions are resolved based on putative fragmentation pathways and chemical composition. In this step, the "difference mass" of the neutral loss ion, instead of the "absolute mass" of the precursor and product ions, may be tested for correspondence to a valid chemical formula since a mass spectrometer such as described herein typically has much better precision than accuracy.

Finally, in step 61, the results are reported to a user (or stored for later use). The results may include calculated product/precursor matches, information regarding detected peaks or other information. The reporting may be performed in numerous alternative ways for instance via a visual display terminal, a paper printout, or, indirectly, by outputting the parameter information to a database on a storage medium for later retrieval by a user. The reporting step may include reporting either textual or graphical information, or both. Reported peak parameters may be either those parameters calculated during the peak detection step or quantities calculated from those parameters and may include, for each of one or more peaks, location of peak centroid, location of point of maximum intensity, peak half-width, peak skew, peak maximum intensity, area under the peak, etc. Other parameters related to signal to noise ratio, statistical confidence in the results, goodness of fit, etc. may also be reported in step 61. The information reported in step 61 may also include characterizing information on one or more analytes and may be derived by comparing the results obtained by the methods described herein to known databases. Such information may include chemical identification of one or more analytes (e.g., ions, molecules or chemical compounds), purity of analytes, identification of contaminating compounds, ions or molecules or, even, a simple notification that an analyte is (or is not) present in a sample at detectable levels.

Section 2. Parameterless Peak Detection in One Independent Variable

The method 40 diagrammed in FIGS. 4A-4B provides a high-level overview of generating automated correlations between all-ions precursor ions and all-ions-fragmentation product ions. However, to fully appreciate the features of the invention, it is necessary to consider significantly more detailed discussion of the step 47 of method 40 as well as additional procedures subsumed therein. The step 47 includes detecting and locating peaks in various extracted-ion-chromatogram (XIC) representations of the precursor ion and product ion data and may itself be regarded as a particular method, which is shown in flowchart form in FIG. 5. Since each XIC includes only the single independent variable of time (e.g., Retention Time), this section is thus directed to detection of peaks in data that includes only one independent variable. Much of the discussion in the present section is adapted from the discussion in the aforementioned United States Patent Application publication 2010/0100336 A1.

Figure 5:
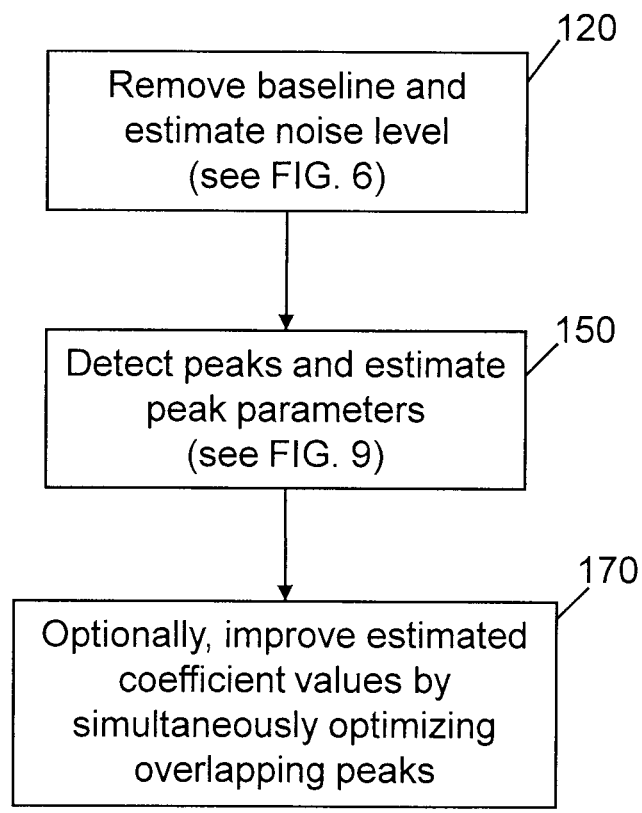
FIG. 5 is a flowchart of a method for automated spectral peak detection and quantification in accordance with an embodiment of the present teachings.
Figure 9:
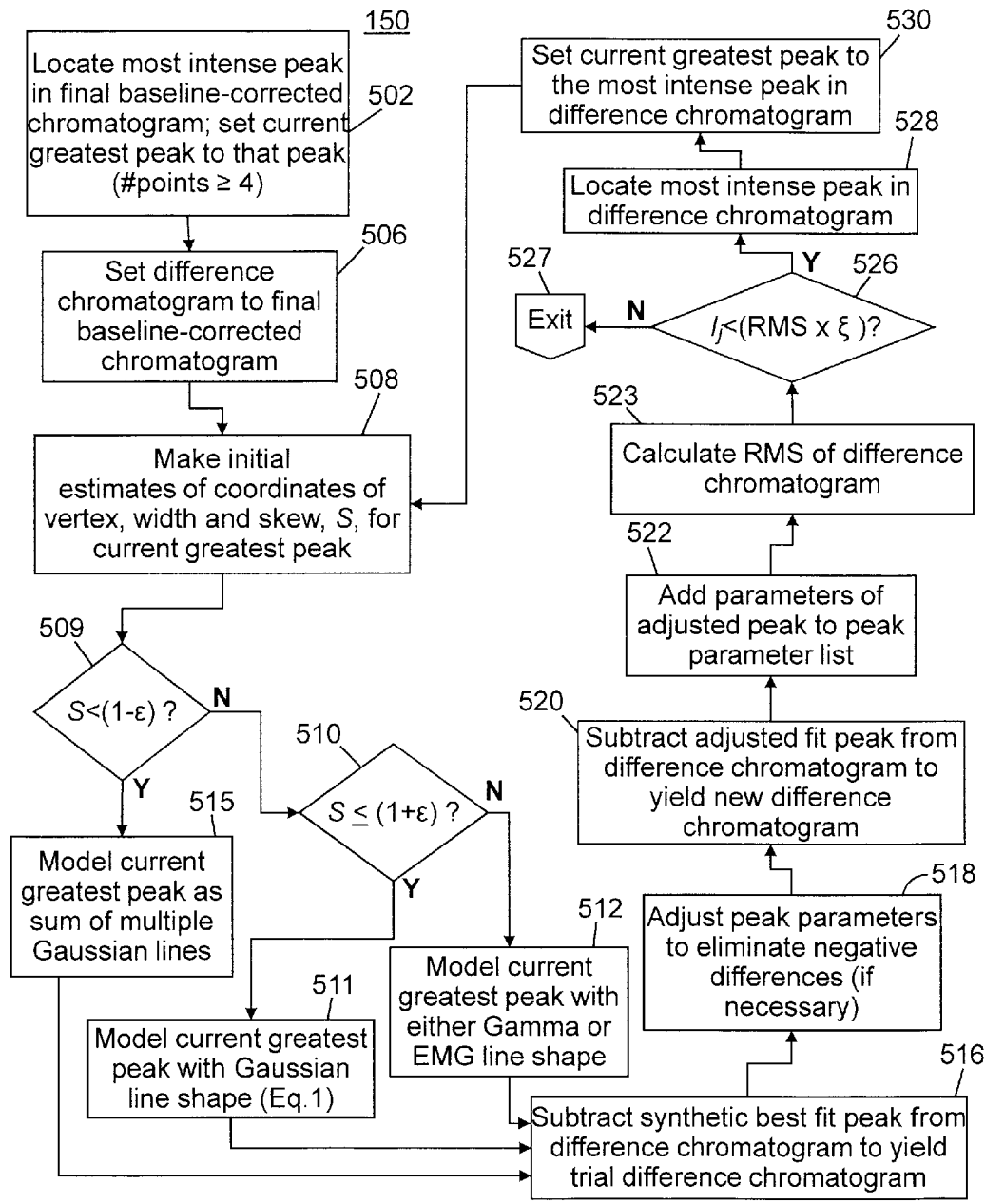
FIG. 9 is a flowchart of a method for automated spectral peak detection and quantification in accordance with an embodiment of the present teachings.

The various sub-procedures or sub-methods in the method 47 may be grouped into three basic stages of data processing, each stage possibly comprising several steps as illustrated in FIG. 5. The first step, step 120, of the method 47 is a preprocessing stage in which baseline features may be removed from the received chromatogram and in which a level of random "noise" of the chromatogram may be estimated, this step being described in greater detail in subsequent FIG. 6. The next step 150, which is described in greater detail in subsequent FIG. 9, is the generation of an initial estimate of the parameters of synthetic peaks, each of which models a positive spectral feature of the baseline corrected chromatogram. Such parameters may relate, for instance, to peak center, width, skew and area of modeled peaks, either in preliminary or intermediate form. The subsequent optional step 170 includes refinement of fit parameters of synthetic peaks determined in the preceding step 150 in order to improve the fit of the peaks, taken as a set, to the baseline corrected chromatogram. The need for such refinement may depend on the degree of complexity or accuracy employed in the execution of modeling in step 150.

The term "model" and its derivatives, as used herein, may refer to either statistically finding a best fit synthetic peak or, alternatively, to calculating a synthetic peak that exactly passes through a limited number of given points. The term "fit" and its derivatives refer to statistical fitting so as to find a best-fit (possibly within certain restrictions) synthetic peak such as is commonly done by least squares analysis. Note that the method of least squares (minimizing the chi-squared metric) is the maximum likelihood solution for additive white Gaussian noise. More detailed discussion of individual method steps and alternative methods is provided in the following discussion and associated figures.

2.1. Baseline Detection

Figure 6:
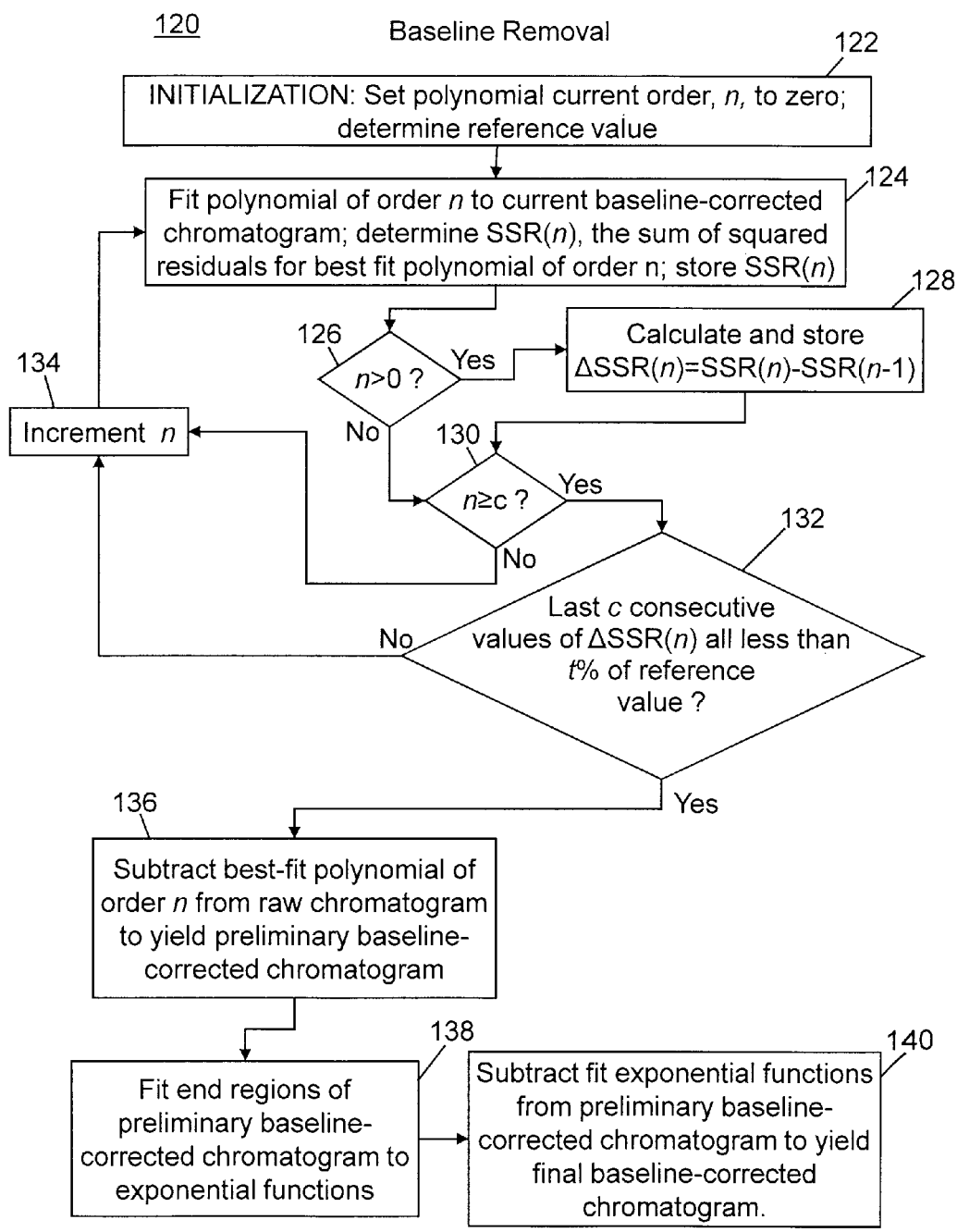
FIG. 6 is a flowchart of a method for automatically removing baseline features and estimating background noise from spectral data in accordance with an embodiment of the present teachings.

A feature of a first stage of the method 47 (FIG. 5) takes note of the concept that (disregarding, for the moment, any chemical or electronic noise) a spectroscopic signal generally consists of signal plus baseline. If one can subtract the baseline correctly, everything that remains must be signal, and should be fitted to some sort of data peak. Thus, the first step 120 comprises determining a correct baseline and removing it from the signal. Sub-steps may include applying a polynomial curve as the baseline curve, and measuring the residual (the difference between the chromatographic data and the computed baseline) as a function of polynomial order. For instance, FIG. 6 illustrates a flowchart of a method 120 for automatically removing baseline features from spectral data in accordance with some embodiments of the invention. The method 120 illustrated in FIG. 6 repeatedly fits a polynomial function to the baseline, subtracts the best fit polynomial function from the chromatogram so as to provide a current baseline-corrected chromatogram, evaluates the quality of the fit, as measured by a sum of squared residuals (SSR), and proceeds until SSR changes, from iteration to iteration, by less than some pre-defined percentage of its original value for a pre-defined number of iterations.

Figure 7:
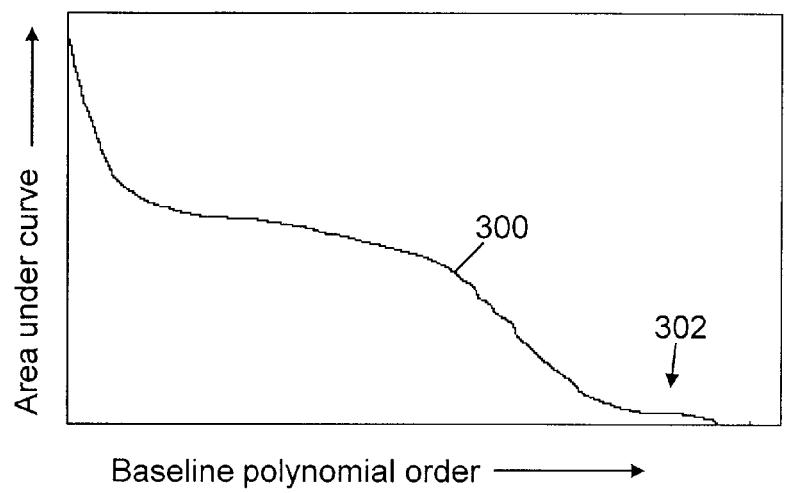
FIG. 7 is a graph of an example of the variation of the calculated area underneath a baseline-corrected spectral curve as a function of the order of polynomial used in fitting the baseline to a polynomial function.

FIG. 7 is an exemplary graph 300 of the variation of the calculated area underneath a baseline-corrected spectral curve as a function of increasing order of the polynomial used in fitting the baseline. FIG. 7 shows that the area initially decreases rapidly as the order of the best fit polynomial increases. This function will go from some positive value at order zero, to a value of zero at some high polynomial order. However, as may be observed from FIG. 7, after most of the baseline curvature has been fit, the area function attains a plateau region 302 for which the change in the function between polynomial orders is some relatively small amount (for instance 5% of its initial value). At this point, the polynomial-fitting portion of the baseline determination routine may be terminated.

To locate the plateau region 302 as indicated in FIG. 7, methods according to the present teachings may repeatedly compute the sum of squared residuals (SSR) for sequential values of polynomial order, each time computing the difference of the SSR ($\Delta$SSR) determined between consecutive polynomial orders. This process is continued until a region is found in which the change ($\Delta$SSR) is less than the pre-defined percentage (for instance, 5%) of a certain reference value determined from the chromatogram for a certain number c (for instance, four) of sequential iterations. The reference value may comprise, for instance, the maximum intensity of the original raw chromatogram. Alternatively, the reference value may comprise the sum of squared values ($SSV_0$) of the original raw chromatogram or some other quantity calculated from the spectral values.

Once it is found that $\Delta$SSR is less than the pre-defined percentage of the reference value for c iterations, then one of the most recent polynomial orders (for instance, the lowest order of the previous four) is chosen as the correct polynomial order. The subtraction of the polynomial with the chosen order yields a preliminary baseline corrected chromatogram, which may perhaps be subsequently finalized by subtracting exponential functions that are fit to the end regions. Although the above-discussion regarding baseline removal is directed to the general case, it should be noted that the mere construction of an XIC representation eliminates signal from most interfering ions. Thus, the magnitudes of baseline offset and baseline curvature are generally minimal for such data representations.

Returning, now, to the discussion of method 120 shown in FIG. 6, it is noted that the first step 122 comprises loop initialization step of setting the order, n, of the baseline fitting polynomial to an initial value of zero and determining a reference value to be used, in a later step 132, for determining when the fitting polynomial provides an adequate fit to the baseline. The reference value may simply be the maximum intensity of the raw chromatogram. Alternatively, the reference value may be some other measure determined from the chromatogram, such as the sum of the squared values (SSV) of the chromatogram.

From step 122, the method 120 proceeds to a step 124, which is the first step in a loop. The step 124 comprises fitting a polynomial of the current order (that is, determining the best fit polynomial of the current order) to the raw chromatogram by the well-known technique of minimization of a sum of squared residuals (SSR). The SSR as a function of n, SSR(n) is stored at each iteration for comparison with the results of other iterations.

From step 124, the method 120 proceeds to a decision step 126 in which, if the current polynomial order n is greater than zero, then execution of the method 120 is directed to step 128 (via the exit branch of step 126 that is labeled "Yes" in FIG. 6) in order to calculate and store the difference of SSR, $\Delta$SSR (n), relative to its value in the iteration just prior. In other words, $\Delta$SSR(n)=SSR(n)−SSR(n−1). The value of $\Delta$SSR(n) may be taken a measure of the improvement in baseline fit as the order of the baseline fitting polynomial is incremented to n. If it is determined, in step 126, that it is not true that the current polynomial order n is greater than zero, then execution of the method 120 is directed to step 130 (via the exit branch of step 126 that is labeled "No"), thereby bypassing the step 128 when n=0 (see FIG. 6).

The iterative loop defined by all steps from step 124 through step 132, inclusive, proceeds until SSR changes, from iteration to iteration, by less than some pre-defined percentage, t %, of the reference value for a pre-defined integer number, c, of consecutive iterations. Thus, the number of completed iterations, integer n, is compared to c in step 130. If n≥c, then the method branches to step 132, in which the last c values of $\Delta$SSR(n) are compared to the reference value. However, in the alternative situation (n<c), there are necessarily fewer than c recorded values of $\Delta$SSR(n), and step 132 is bypassed, with execution being directed to step 134, in which the integer n is incremented by one.

The sequence of steps from step 124 up to step 132 (going through step 128, as appropriate) is repeated until it is determined, in step 132, that the there have been c consecutive iterations in which the SSR value has changed by less than t % of the reference value. At this point, the polynomial portion of baseline correction is completed and the method branches to step 136, in which the final polynomial order is set and a polynomial of such order is subtracted from the raw chromatogram to yield a preliminary baseline-corrected chromatogram.

Figure 8:
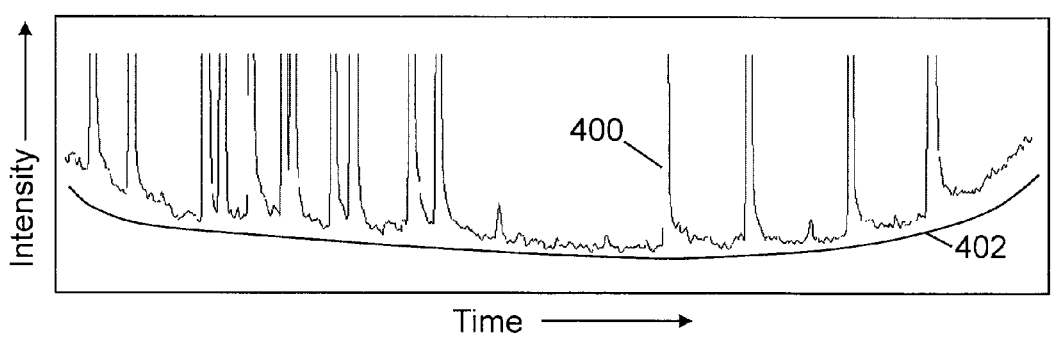
FIG. 8 is an example of a preliminary baseline corrected spectral curve prior to fitting the end regions to exponential functions and an example of the baseline comprising exponential fit functions.

The polynomial baseline correction is referred to as "preliminary" since edge effects may cause the polynomial baseline fit to be inadequate at the ends of the data, even though the central region of the data may be well fit. FIG. 8 shows an example of such a preliminary baseline corrected chromatogram 400. The residual baseline curvature within the end regions (for instance, the leftmost and rightmost 20% of the chromatogram) of the chromatogram 400 are well fit by a sum of exponential functions (one for each end region), the sum of which is shown in FIG. 8 as curve 402. Either a normal or an inverted (negated) exponential function may be employed, depending on whether the data deviates from zero in the positive or negative direction. This correction may be attempted at one or both ends of the chromatogram. Thus, the method 120 proceeds to step 138 which comprises least squares fitting of the end region baselines to exponential functions, and then to step 140 which comprises subtraction of these functions from the preliminary baseline-corrected chromatogram to yield the final baseline corrected chromatogram. These steps yield a final baseline-corrected chromatogram.

2.2. Peak Detection

At this point, after the application of the steps outlined above, the baseline is fully removed from the data and the features that remain within the chromatogram above the noise level may be assumed to be analyte signals. The methods described in FIG. 9 locate the most intense region of the data, fit it to one of several peak shapes, remove that theoretical peak shape from the experimental data, and then continue to repeat this process until there are no remaining data peaks with a signal-to-noise ratio (SNR) greater than some pre-determined value, s, greater than or equal to unity. The steps of this process are illustrated in detail in FIG. 9 as method 150 and also shown in FIG. 5 as step 150. The pre-defined value, s, may be chosen so as to limit the number of false positive peaks. For instance, if the RMS level of Rayleigh-distributed noise is sigma, then a peak detection threshold, s, of 3 sigma leads to a false detection rate of about 1%.

The method 150, as shown in FIG. 9 is an iterative process comprising initialization steps 502 and 506 and loop steps 508-530 (including loop exit decision step 526) and termination step 527. A new respective peak is located and modeled during each iteration of the loop defined by the sequence of steps 508-530.

The first step 502 of method 150 comprises locating the most intense peak in the final baseline-corrected chromatogram and setting a program variable, current greatest peak, to the peak so located. It is to be kept in mind that, as used in this discussion, the acts of locating a peak or chromatogram, setting or defining a peak or chromatogram, performing algebraic operations on a peak or chromatogram, etc. implicitly involve either point-wise operations on sets of data points or involve operations on functional representations of sets of data points. Thus, for instance, the operation of locating the most intense peak in step 502 involves locating all points in the vicinity of the most intense point that are above a presumed noise level, under the proviso that the total number of points defining a peak must be greater than or equal to four. Also, the operation of "setting" a program variable, current greatest peak, comprises storing the data of the most intense peak as an array of data points.

From step 502, the method 150 proceeds to second initialization step 506 in which another program variable, "difference chromatogram" is set to be equal to the final baseline-corrected chromatogram (see step 140 of method 120, FIG. 6). The difference chromatogram is a program variable that is updated during each iteration of the loop steps in method 150 so as to keep track of the chromatogram resulting from subtraction of all prior-fitted peaks from the final baseline-corrected chromatogram. As discussed later in this document, the difference chromatogram is used to determine when the loop is exited under the assumption that, once all peaks have been located and modeled, the difference chromatogram will consist only of "noise".

Figure 11:
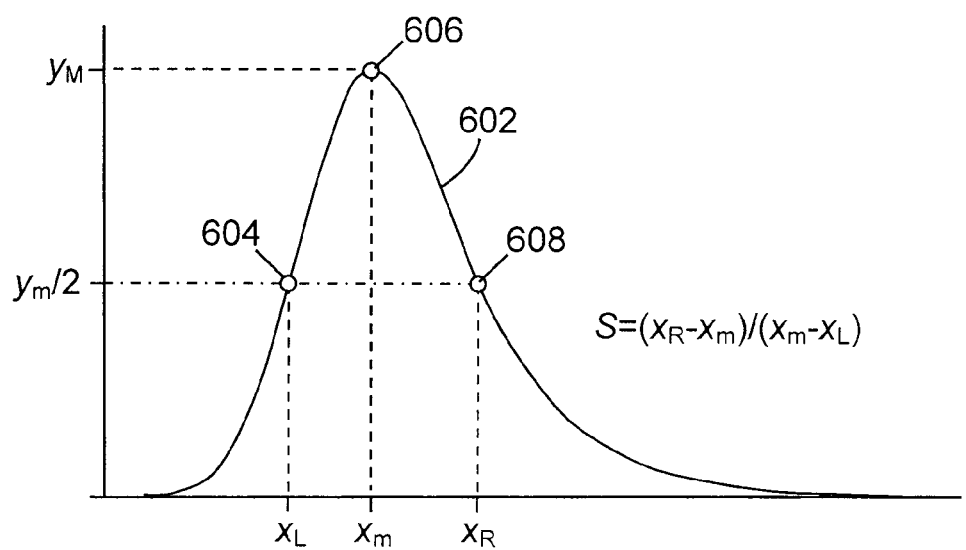
FIG. 11 a graph of a hypothetical skewed spectral peak depicting a method in accordance with the present teachings for obtaining three points on the spectral peak to be used in an initial estimate of skew and for preliminary peak fitting.

Subsequently, the method 150 enters a loop at step 508, in which initial estimates are made of the coordinates of the peak maximum point and of the left and right half-height points for the current greatest peak and in which peak skew, S is calculated. The method of estimating these co-ordinates is schematically illustrated in FIG. 11 and is discussed in greater detail later with respect to FIGS. 14A-14B. Letting curve 602 of FIG. 11 represent the current greatest peak, then the co-ordinates of the peak maximum point 606, left half-height point 604 and right half-height point 608 are, respectively, $(x_m, y_m)$, $(x_L, y_m/2)$ and $(x_R, y_m/2)$. The peak skew, S, is then defined as: $S=(x_R-x_m)/(x_m-x_L)$.

In steps 509 and 510, the peak skew, S, may be used to determine a particular form (or shape) of synthetic curve (in particular, a distribution function) that will be subsequently used to model the current greatest peak. Thus, in step 509, if $S<(1-\epsilon)$, where $\epsilon$ is some pre-defined positive number, such as, for instance, $\epsilon=0.05$, then the method 150 branches to step 515 in which the current greatest peak is modeled as a sum of two or more Gaussian distribution functions (in other words, two Gaussian lines). Otherwise, in step 510, if $S \leq (1+\epsilon)$, then the method 150 branches to step 511 in which a (single) Gaussian distribution function is used as the model peak form with regard to the current greatest peak. Otherwise, the method 150 branches to step 512, in which either a gamma distribution function or an exponentially modified Gaussian (EMG) or some other form of distribution function is used as the model peak form. Alternatively, the current greatest peak could be modeled as a sum of two or more Gaussian distribution functions in step 512. A non-linear optimization method such as the Marquardt-Levenberg Algorithm (MLA) or, alternatively, the Newton-Raphson algorithm may be used to determine the best fit using any particular line shape. After either step 511, step 512 or step 515, the synthetic peak resulting from the modeling of the current greatest peak is removed from the chromatogram data (that is, subtracted from the current version of the "difference chromatogram") so as to yield a "trial difference chromatogram" in step 516. Additional details of the gamma and EMG distribution functions and a method of choosing between them are discussed in greater detail, partially with reference to FIG. 13, later in this document.

Occasionally, the synthetic curve representing the statistical overall best-fit to a given spectral peak will lie above the actual peak data within certain regions of the peak. Subtraction of the synthetic best fit curve from the data will then necessarily introduce a "negative" peak artifact into the difference chromatogram at those regions. Such artifacts result purely from the statistical nature of the fitting process and, once introduced into the difference chromatogram, can never be subtracted by removing further positive peaks. However, physical constraints generally require that all peaks should be positive features. Therefore, an optional adjustment step is provided as step 518 in which the synthetic peak parameters are adjusted so as to minimize or eliminate such artifacts.

In step 518 (FIG. 9), the solution space may be explored for other fitted peaks that have comparable squared differences but result in residual positive data. A solution of this type is selected over a solution that gives negative residual data. Specifically, the solution space may be incrementally walked so as to systematically adjust and constrain the width of the synthetic peak at each of a set of values between 50% and 150% of the width determined in the original unconstrained least squares fit. After each such incremental change in width, the width is constrained at the new value and a new least squared fit is executed under the width constraint. The positive residual (the average difference between the current difference chromatogram and the synthetic peak function) and chi-squared are calculated and temporarily stored during or after each such constrained fit. As long as chi-squared doesn't grow beyond a certain multiple of its initial value, for instance 3-times its initial value, the search continues until the positive residual decreases to below a certain limit, or until the limit of peak width variation is reached. This procedure results in an adjusted synthetic fit peak which, in step 520, is subtracted from the prior version of the difference chromatogram so as to yield a new version of the difference chromatogram (essentially, with the peak removed). In step 522, information about the most recently adjusted synthetic peak, such as parameters related to peak form, center, width, shape, skew, height and/or area are stored.

In step 523, the root-of-the-mean squared values (root-mean-square or RMS) of the difference chromatogram is calculated. The ratio of this RMS value to the intensity of the most recently synthesized peak may be taken as a measure of the signal-to-noise (SNR) ratio of any possibly remaining peaks. As peaks continue to be removed (that is, as synthetic fit peaks are subtracted in each iteration of the loop), the RMS value of the difference chromatogram approaches the RMS value of the noise.

Step 526 is entered from step 523. In step 526, as each tentative peak is found, its maximum intensity, I, is compared to the current RMS value, and if $I<(RMS \times \xi)$ where $\xi$ is a certain pre-defined noise threshold value, greater than or equal to unity, then further peak detection is terminated. Thus, the loop termination decision step 526 utilizes such a comparison to determine if any peaks of significant intensity remain distinguishable above the system noise. If there are no remaining significant peaks present in the difference chromatogram, then the method 150 branches to the final termination step 527. However, if data peaks are still present in the residual chromatogram, the calculated RMS value will be larger than is appropriate for random noise and at least one more peak must be fitted and removed from the residual chromatogram. In this situation, the method 150 branches to step 528 in which the most intense peak in the current difference chromatogram is located and then to step 530 in which the program variable, current greatest peak, is set to the most intense peak located in step 528. The method then loops back to step 508, as indicated in FIG. 9.

Now that the overall set of steps in the method 150 have been described, the process that is used to model individual spectral features is now discussed in greater detail. Traditional spectral peak fitting routines generally model spectral features using either a Gaussian or Lorentzian forms (commonly referred to as peak shapes or line shapes) and tend to either use one preferred line shape throughout the fitting procedure or to query a user as to which line shape to use. Although any arbitrary peak shape can be modeled with a sum of Gaussians (perhaps requiring some Gaussians with negative intensities), the inventors have observed that commonly occurring natural peak shapes (especially in chromatographic spectral data) include Gaussians or even Gamma-distribution-like functions with tailing or leading edges. Therefore, methods in accordance with the present teachings may employ a library of peak shapes containing at least four curves (and possibly others) to model observed peaks: a Gaussian for peaks that are nearly symmetric; a sum of two Gaussians for peaks that have a leading edge (negative skewness); a and either an exponentially modified Gaussian or a Gamma distribution function for peaks that have a tailing edge (positive skewness).

The modeling of spectral peaks with Gaussian line shapes is well known and will not be described in great detail here. Methods in accordance with the present teachings may use a Gaussian functional form that utilizes exactly three parameters for its complete description, these parameters usually being taken as area A, mean $\mu$ and variance $\sigma^2$ in the defining equation:

$$I(x; A, \mu, \sigma^2) = \frac{A}{\sigma\sqrt{2\pi}} \exp\left(-\frac{(x-\mu)^2}{2\sigma^2}\right). \quad \text{Eq. 1}$$

in which x is the variable of spectral dispersion (generally the independent variable or abscissa of an experiment or spectral plot) such as wavelength, frequency, or time and I is the spectral ordinate or measured or dependent variable, possibly dimensionless, such as intensity, counts, absorbance, detector current, voltage, etc. Note that a normalized Gaussian distribution (having a cumulative area of unity and only two parameters—mean and variance) would model, for instance, the probability density of the elution time of a single molecule. In the three-parameter model given in Eq. 1, the scale factor A may be taken as the number of analyte molecules contributing to a peak multiplied by a response factor.

As is known, the functional form of Eq. 1 produces a symmetric line shape (skew, S, equal to unity) and, thus, step 511 in the method 150 (FIG. 9) utilizes a Gaussian line shape when the estimated peak skew is in the vicinity of unity, that is when $(1-\epsilon) \leq S \leq (1+\epsilon)$ for some positive quantity $\epsilon$. In the illustration shown in FIG. 9, the quantity $\epsilon$ is taken as 0.05, but it could be any other pre-defined positive quantity. A statistical fit may performed within a range of data points established by a pre-defined criterion. For instance, the number of data points to be used in the fit may be calculated by starting with a pre-set number of points, such as 12 points and then adjusting, either increasing or decreasing, the total number of data points based on an initial estimated peak width. Preferably, downward adjustment of the number of points to be used in the fit does not proceed to less than a certain minimum number of points, such as, for instance, five points.

Alternatively, the fit may be mathematically anchored to the three points (i.e., the peak maximum point 606, left half-height point 604 and right half-height point 608) shown in FIG. 11. Alternatively, the range of the fit may be defined as all points of the peak occurring above the noise threshold. Still further alternatively, the range may be defined via some criterion based on the intensities of the points or their intensities relative to the peak maximum point 606, or even on criterion based wholly or in part on calculation time. Such choices will depend on the particular implementation of the method, the relative requirements for calculation speed versus accuracy, etc.

Figure 12:
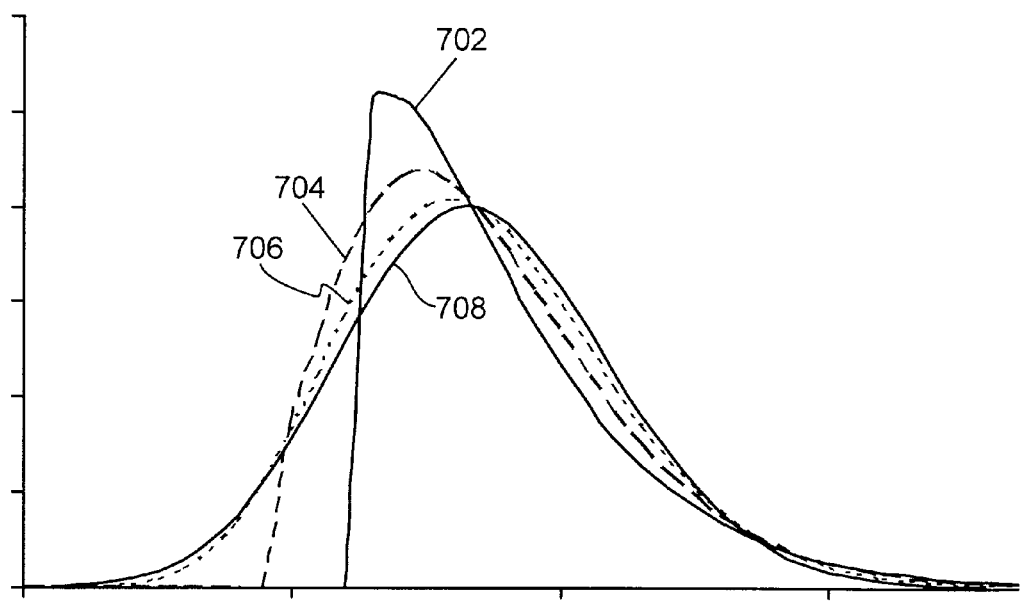
FIG. 12 a graph of a set of gamma distribution functions having different values of shape parameter M, illustrating a fashion by such functions may be used to synthetically fit skewed spectral peaks.

If $S > (1+\epsilon)$, then the data peak is skewed so as to have an elongated tail on the right-hand side. This type of peak may be well modeled using either a line shape based on either the Gamma distribution function or on an exponentially modified Gaussian (EMG) distribution function. Examples of peaks that are skewed in this fashion (all of which are synthetically derived Gamma distributions) are shown in the set of four different Gamma distribution functions 700 of FIG. 12. If the peaks in FIG. 12 are taken to be chromatograms, then the abscissa in each case is in the units of time, increasing towards the right.

The general form of the Gamma distribution function, as used herein, is given by:

$$I(x; A, x_0, M, r) = A \frac{r^M (x-x_0)^{M-1} e^{-r(x-x_0)}}{\Gamma(M)}, x \geq x_0 \quad \text{Eq. 2}$$

in which the dependent and independent variables are x and I, respectively, as previously defined, $\Gamma(M)$ is the Gamma function, defined by $$\Gamma(M) = \int_0^\infty u^{M-1} e^{-u} du$$

and are A, $x_0$, M and r are parameters, the values of which are calculated by methods of the present teachings. Note that references often provide this in a "normalized" form (i.e., a probability density function), in which the total area under the curve is unity and which has only three parameters. However, as noted previously herein, the peak area parameter A may be taken as corresponding to the number of analyte molecules contributing to the peak multiplied by a response factor.

The inventors consider that a chromatographic peak of a single analyte exhibiting peak tailing may be modeled by a four-parameter Gamma distribution function, wherein the parameters may be inferred to have relevance with regard to physical interaction between the analyte and the chromatographic column. In this case, the Gamma function may be written as:

$$I(t; A, t_0, M, r) = A \frac{r^M (t-t_0)^{M-1} e^{-r(t-t_0)}}{\Gamma(M)} \quad t \geq t_0 \qquad \text{Eq. 2a}$$

in which t is retention time (the independent variable), A is peak area, $t_0$ is lag time and M is the mixing number. Note that if M is a positive integer then $\Gamma(M)=(M-1)!$ and the distribution function given above reduces to the Erlang distribution. The adjustable parameters in the above are A, $t_0$, M and r. FIG. 12 illustrates four different Gamma distribution functions 700 for which the only difference is a change in the value of the mixing parameter, M. For curves 702, 704, 706 and 708, the parameter M is given by M=2, M=5, M=20 and M=100, respectively. In the limit of high M, the Gamma function approaches the form of a Gaussian function.

The general, four-parameter form of the exponentially modified Gaussian (EMG) distribution, as used in methods according to the present teachings, is given by a function of the foam:

$$I(x; A, x_0, \sigma^2, \tau) = A \int_{-\infty}^{x} \frac{1}{\sigma \sqrt{2\pi}} e^{-(u-x_0)^2/2\sigma^2} \frac{1}{\tau} e^{-(x-u)/\tau} du \qquad \text{Eq. 3}$$

$(x \geq 0; \tau > 0).$

Thus, the EMG distribution used herein is defined as the convolution of an exponential distribution with a Gaussian distribution. In the above Eq. 3, the independent and dependent variables are x and I, as previously defined and the parameters are A, $t_0$, $\sigma^2$, and r. The parameter A is the area under the curve and is proportional to analyte concentration and the parameters $t_0$ and $\sigma^2$ are the centroid and variance of the Gaussian function that modifies an exponential decay function. An exponentially-modified Gaussian distribution function of the form of Eq. 3 may be used to model some chromatographic peaks exhibiting peak tailing. In this situation, the general variable x is replaced by the specific variable time t and the parameter $x_0$ is replaced by $t_0$.

Figure 13:
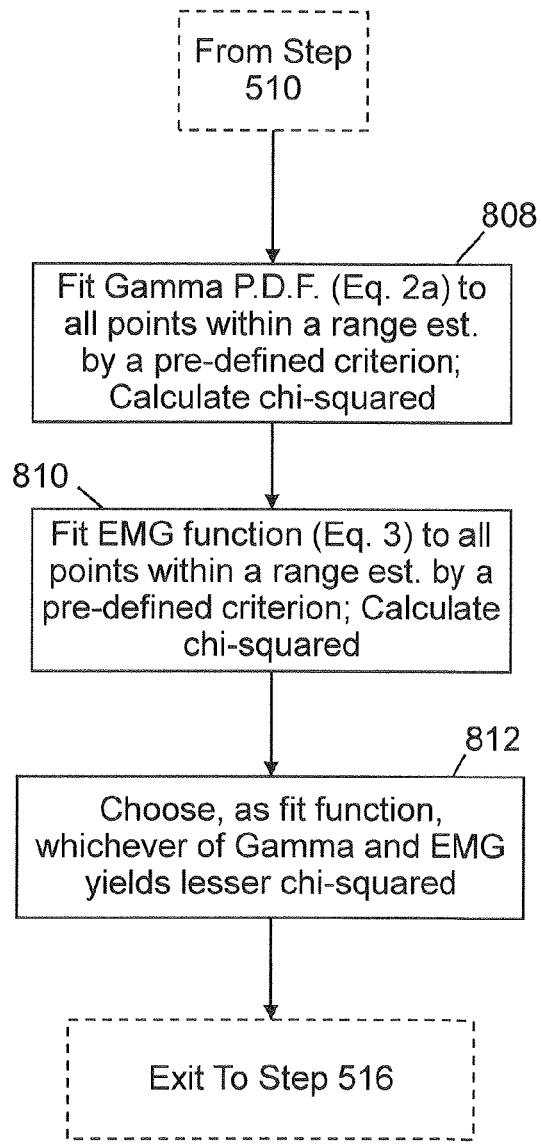
FIG. 13 is a flowchart illustrating a method for choosing between line shapes used for fitting.

FIG. 13 illustrates, in greater detail, various sub-steps that may be included in the step 512 of the method 150 (see FIG. 5 and FIG. 9) within embodiments in accordance with the present teachings. More generally, FIG. 13 outlines an exemplary method for choosing between line shape forms in the modeling and fitting of an asymmetric spectral peak. The method 512 illustrated in FIG. 13 may be entered from step 510 of the method 150 (see FIG. 9).

When method 512 is entered from step 510 (see FIG. 9), the skew, S, is greater than (1+ε), because the respective "No" branch has previously been executed in each of steps 509 and 510 (see FIG. 9). For instance, if s is set to 0.05, then the skew is greater than 1.05. When S>(1+ε), both the EMG distribution (in the form of Eq. 3) and the Gamma distribution may be fit to the data in steps 810 and 808, respectively, and one of the two distributions may be selected as a model of better fit on the basis of the squared difference (chi-squared statistic).

In the two steps, 808 and 810 of the method 512, first one line shape and then an alternative line shape is fitted to the data and a chi-squared statistic is calculated for each. The fit is performed within a range of data points established by a pre-defined criterion. For instance, the number of data points to be used in the fit may be calculated by starting with a pre-set number of points, such as 12 points and then adjusting, either increasing or decreasing, the total number of data points based on an initial estimated peak width. Preferably, downward adjustment of the number of points to be used in the fit does not proceed to less than a certain minimum number of points, such as, for instance, five points. In step 808, a Gamma probability distribution function (P.D.F.) is fit to all points within the range. From step 808, the method 512 (FIG. 13) proceeds to step 810, in which an exponentially modified Gaussian function is fit to the points within the range.

Alternatively, the fit may be mathematically anchored to the three points (i.e., the peak maximum point 606, left half-height point 604 and right half-height point 608) shown in FIG. 11. Alternatively, the range may be defined as all points of the peak occurring above the noise threshold. Still further alternatively, the range may be defined via some criterion based on the intensities of the points or their intensities relative to the peak maximum point 606, or even on criterion based wholly or in part on calculation time. Such choices will depend on the particular implementation of the method, the relative requirements for calculation speed versus accuracy, etc. Finally, after execution of both steps 808 and 810, the fit function is chosen in step 812 as that which yields the lesser chi-squared. The method 512 then outputs the results or exits to step 516 of method 150 (see FIG. 9).

Figure 14A:
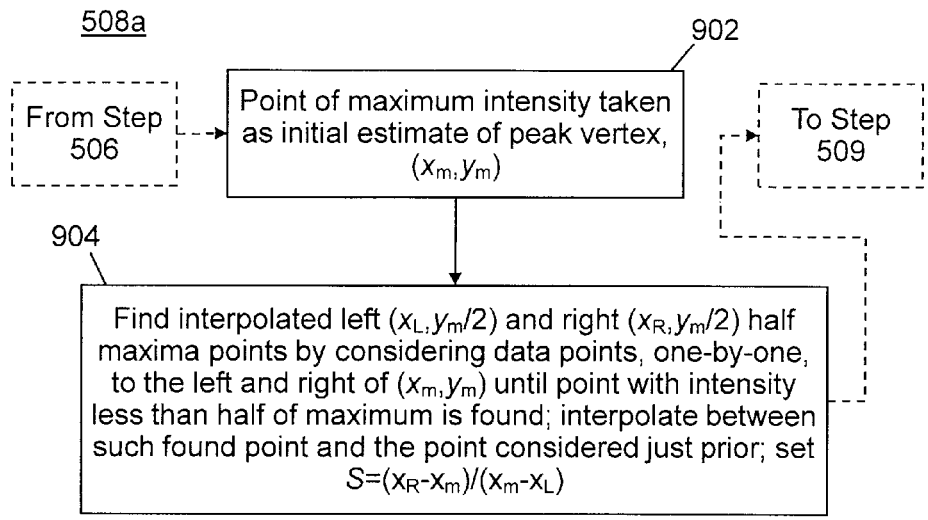
FIG. 14A is a flowchart illustrating steps for estimating coordinates of points at a peak maximum and along flanks of the peak at half-height, according to a method of the present teachings.
Figure 14B:
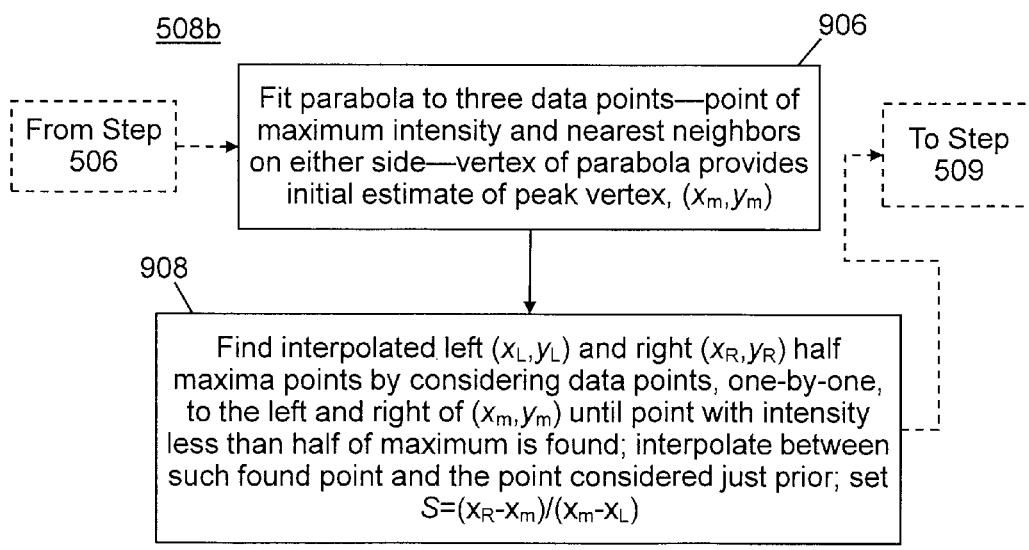
FIG. 14B is a flowchart illustrating alternative steps for estimating coordinates of points at a peak maximum and along flanks of the peak at half-height, according to a method of the present teachings.

FIGS. 14A-14B are flowcharts that respectively illustrate, in greater detail, alternative sets of sub-steps that may be included in the step 508 of the method 150 (see FIG. 5 and FIG. 9) within embodiments in accordance with the present teachings. More generally, FIGS. 14A and 14B illustrate steps for estimating coordinates of points at a peak maximum and along flanks of the peak at half-height, according to a first exemplary method, method 508a (FIG. 14A) as well as according to an alternative exemplary method, method 508b (FIG. 14B) in accordance with the present teachings. Each of the two methods 508a (FIG. 14A) and 508b (FIG. 14B) may be entered from step 506 of method 150 (FIG. 9) and may output data or exit to step 509 of method 150. Upon detection of a peak, the point of maximum intensity (e.g., point 606 of FIG. 11) may be taken as an initial estimate of the peak vertex $(x_m, y_m)$ as in step 902 of method 508a. Alternatively, the sample of maximum intensity and its two nearest neighbors may be fit to a parabola as in step 906 of method 508b, and then the vertex of the parabola used to provide an estimate of the interpolated peak vertex (which in general does not exactly coincide with a data point of a chromatogram). Next, in either step 904 of method 508a or step 908 of method 508b, the left and right half maxima of the detected peak (e.g., points 604 and 608, respectively, of FIG. 11) are estimated by examining the sample values to the left and right (respectively), scanning outward from the peak vertex until encountering a value that is less than one-half the interpolated maximum value. Interpolated values of the left and right half-maxima are determined by fitting a line to sample points whose intensities lie above and below one-half the maximum intensity and finding the x-axis coordinate (either $x_L$ or $x_R$—see FIG. 11) of the point on the line that passes through the half-maximum intensity. Then, the estimated peak skew, S, is calculated as $S=(x_R-x_m)/(x_m-x_L)$.

Returning, once again, to the method 47 as shown in FIG. 5, it is noted that, after all peaks have been fit in step 150, the next optional step, step 170 comprises refinement of the initial parameter estimates for multiple detected chromatographic peaks. Refinement comprises exploring the space of N parameters (the total number of parameters across all peaks, i.e. 4 for each Gamma/EMG and 3 for each Gaussian) to find the set of values that minimizes the sum of squared differences between the observed and model chromatogram. Preferably, the squared difference may be calculated with respect to the portion of the chromatogram comprising multiple or overlapped peaks. It may also be calculated with respect to the entire chromatogram. The model chromatogram is calculated by summing the contribution of all peaks estimated in the previous stage. The overall complexity of the refinement can be greatly reduced by partitioning the chromatogram into regions that are defined by overlaps between the detected peaks. In the simplest case, none of the peaks overlap, and the parameters for each individual peak can be estimated separately.

The refinement process continues until a halting condition is reached. The halting condition can be specified in terms of a fixed number of iterations, a computational time limit, a threshold on the magnitude of the first-derivative vector (which is ideally zero at convergence), and/or a threshold on the magnitude of the change in the magnitude of the parameter vector. Preferably, there may also be a "safety valve" limit on the number of iterations to guard against non-convergence to a solution. As is the case for other parameters and conditions of methods of the present teachings, this halting condition is chosen during algorithm design and development and not exposed to the user, in order to preserve the automatic nature of the processing. At the end of refinement, the set of values of each peak area along with a time identifier (either the centroid or the intensity maximum) is returned. The entire process is fully automated with no user intervention required.

Section 3. Application to Three-Variable LC-MS Data

The foregoing description has mainly dealt with characterizing peaks in spectral data comprising just a single independent variable (i.e., a time-related independent variable for XIC or TIC data). For example, several schematic extracted ion chromatograms are illustrated in FIG. 15A by dotted lines residing at respective mass-to-charge values indicated by sections m1, m2, m3 and m4 as well as at mass-to-charge values indicated by sections mf1, mf2 and mf3. Subsequent to execution of the methods discussed in Section 2 above, each such XIC is defined by the set of synthetic peaks calculated by those methods. The hypothetical synthetic extracted ion chromatograms schematically shown in FIG. 15A illustrate elution of various ionized chemical constituents at closely-spaced times rt1, rt2, rt3 and rt4. Although illustrated as separated times, one or more of the times rt1, rt2, rt3 and rt4 could even be identical to one another, such that the various chemical constituents are co-eluting constituents. It should be noted that the mass scale (i.e., m/z scale) relating to product ion scans in FIG. 15A is not a simple extension of the mass scale relating respectively relating to precursor ion scans. In fact, the two mass scales may overlap one another but are not necessarily identical to one another.

The set of extracted ion chromatograms indicated by sections m1, m2, m3 and m4 in FIG. 15A could be algebraically summed so as to yield a reconstructed total ion chromatogram (not shown). Likewise, the synthetic peak intensities provided by the peak detection and fitting routines described above could be projected onto the time sections shown at times rt1, rt2, rt3 and rt4 in order to generate reconstructed mass spectra (reconstructed "scans"). Reconstructed mass spectra are illustrated by the solid-line curves in FIG. 15A and FIG. 15C. In accordance with the present teachings the reconstructed scans are generated by including all masses that produce a chromatographic peak at the time corresponding to the scan, lie within the linewidth of said peak, and were collected under identical scan filters. Thus, every ion present in a reconstructed scan is known to contribute to a chromatographic peak, whose apex is nearby but not necessarily at the time of the scan.

3.1. Line Shape Reproduction by Parameterless Peak Detection Methods

Figure 16:
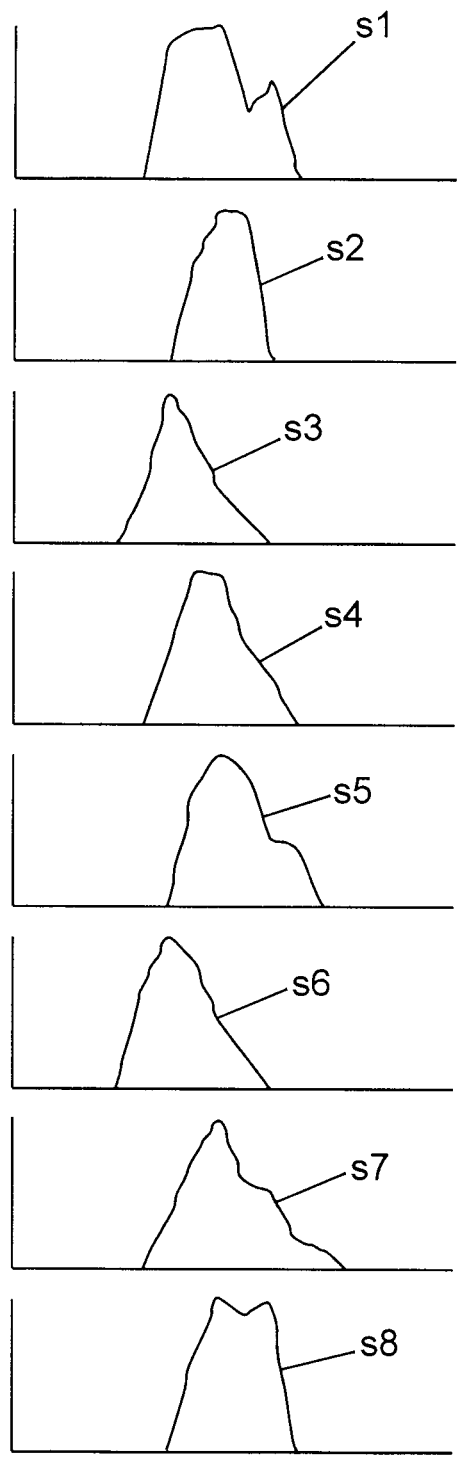
FIG. 16 is a set of plots of several observed line shapes in various extracted ion chromatograms obtained from LC/MS data covering the 1.7-second elution of a single mass chromatographic peak (e.g., a total ion chromatogram peak) of a 500 nM solution of the drug Buspirone.

The extracted ion chromatogram (XIC) peak shapes for components that elute at similar times are not all the same, neither are they all different. FIG. 16 shows results from a typical situation, in which the peak shapes in various extracted ion chromatograms fall into several groups of patterns indicated by the peak profiles s1-s8. The data from which these profiles were generated was obtained using an instrumental system similar to that shown in FIG. 2 and were obtained during the 6-second elution of a single mass chromatographic peak (e.g., a total ion chromatogram peak) of a 500 nM solution of the drug Buspirone. The profiles s1-s8 correspond to different respective m/z ranges obtained from the all-ions fragment data.

Comparison of the illustrated XIC peak profiles in FIG. 15A illustrates how precursor-ion profiles may be similar in shape to the profiles of product ions relating to elution of the same compound and, also, how profiles relating to elution of different compounds may be expected to have different respective shapes. Since the chemistry and physics that determine the chromatographic peak shape are unique for each molecule and cease when the molecule exits the column, one can expect that XICs having similar shapes may be related. A stronger statement can be made that XICs that have different shapes are not fragments of the same precursor. By using Parameterless Peak Detection (PPD) techniques, as described in Section 2 herein, to characterize the peak shape, small differences in shape can be encoded in a correlation vector (described in more detail following). This can be enhanced by additional smoothing after the peak is detected (but not before, since prior smoothing can smooth a noise spike into a peak). Step 59 of method 40 (FIG. 4A) is the cross-correlation step which is described in more detail in the following section 3.2. Cross Correlation Calculations in all Ions Fragmentation Overall cross-correlation scores (CCS) in accordance with the present teachings are calculated (i.e., in step 59 of method 40) according to the following strategy. For each mass in the experimental data that is found to form a chromatographic peak by PPD as described in Section 2, the cross correlation of every mass with every other mass is computed. In the present context, the term "peak" refers simply to masses that have non-zero intensity values for several contiguous or nearly contiguous scans (for example, the scans at times rt1, rt2, rt3 and rt4 illustrated in FIGS. 15A, 15B and FIG. 15C) of the same filter type. Each cross-correlation score is calculated as a weighted average of a peak shape correlation score (calculated in terms of a time-versus-intensity for each mass that forms a recognized peak), a mass defect correlation score (for differences along the m/z axis) and an optional peak width correlation score as described below. If a calculated overall correlation score is such that a match between masses is recognized, then an MS/MS spectrum is reconstructed with the mass of the precursor-ion member as parent and masses from the all-ions fragmentation step as product ions.

Methods in accordance with the present teachings use a trailing retention time window to calculate peak-shape cross correlations. The methods make use of a numerical array including mass, intensity, and scan number values for every mass that forms a chromatographic peak. As described in Section 2, Parameterless Peak Detection (PPD) is used to calculate a peak shape for each mass component. This shape may be a simple Gaussian or Gamma function peak, or it may be a sum of many Gaussian or Gamma function shapes, the details of which are stored in a peak parameter list. Once the component peak shape has been characterized by an analytical function (which may be a sum of simple functions), the problem of calculating a dot-product correlation is greatly simplified. Time offsets (e.g., Δτ, see FIG. 15A) in the original data are no longer relevant, since the analytic functions for two different mass components may be sampled at the same arbitrary points. Once this is accomplished, it is trivial to calculate a cross correlation, here considered as a simple vector product ("dot product"). These cross correlations are normalized by also calculating, and dividing by, the autocorrelation values. Consequently, the peak shape correlation (PSC) between two peak profiles, p1 and p2 (denoted, functionally as p1(t) and p2(t), where t represents a time variable, may be calculated as $$PSC(p1, p2) = \frac{\sum_{j=jmin}^{j=jmax} [p1(t_j) \times p2(t_j)]}{\left\{\sum_{j=jmin}^{j=jmax} p1(t_j)^2\right\}^{1/2} \left\{\sum_{j=jmin}^{j=jmax} p2(t_j)^2\right\}^{1/2}} \quad \text{Eq. 4}$$

in which the time axis is considered as divided into equal width segments, thus defining indexed time points, $t_j$, ranging from a practically defined lower time bound, $t_{j\ min}$, to a practically defined upper time bound, $t_{j\ max}$. Accordingly, the quantity PSC can theoretically have a range of 1 (perfect correlation) to −1 (perfect anti-correlation), but since negative going chromatographic peaks are not detected by PPD (by design) the lower limit is effectively zero. For example, the lower and upper time bounds, $t_{j\ min}$, and, $t_{j\ max}$, may be set in relation to each precursor ion. In such a case, the time values are chosen so as to sample intensities a fixed number of times (for instance, between roughly seven and fifteen times, such as eleven times) across the width of a precursor ion peak. The masses to be correlated with the chosen precursor ion then use the same time points. This means that if these masses form a peak at markedly different times, the intensities will be essentially zero. Partially overlapped peaks will have some zero terms.

Figure 17:
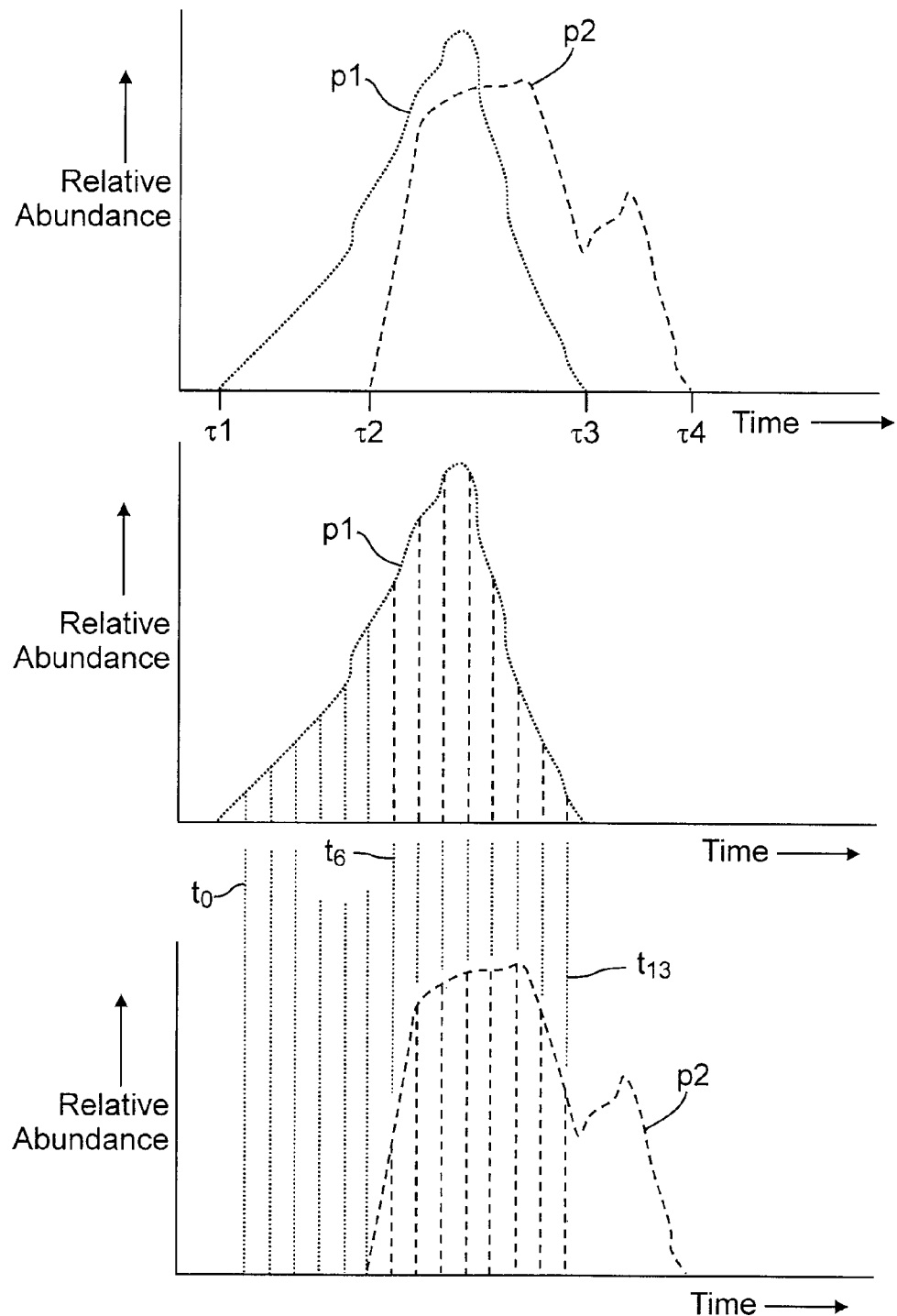
FIG. 17 is a schematic illustration of two peaks having differing line shapes illustrating a method of calculating a cross-correlation score as a dot product.

FIG. 17 graphically illustrates calculation of a dot product cross-correlation score in this fashion. In FIG. 17, two XIC peak profiles p1 and p2 are reproduced from FIG. 15A. Peak p1 has appreciable intensity above baseline only between time points τ1 and τ3 and peak p2 has appreciable intensity only between time points τ2 and τ4. Assume that peak profile p1 corresponds to a precursor ion (or precursor ion candidate) and that peak p2 corresponds to a product ion (or product ion candidate). As discussed above, to calculate the dot-product cross correlation score between these two peaks, the retention time axis may be considered as being divided into several equal segments between time points r1 and r3, thereby defining, in this example, indexed time points $t_j$ where (0≤j≤13). The two peak profiles are shown separately in the lowermost two graphs of FIG. 17 in association with vertical lines representing the various indexed time points along the retention time axis. In this representation, peak p2 only has appreciable intensity between the points $t_6$ and $t_{(13)}$. Thus, in this example, the peak shape correlation is given by $$PSC(p1, p2) = \frac{\sum_{j=0}^{j=13} [p1(t_j) \times p2(t_j)]}{\left\{\sum_{j=0}^{j=13} p1(t_j)^2\right\}^{1/2} \left\{\sum_{j=0}^{j=13} p2(t_j)^2\right\}^{1/2}}$$

Under such a calculation, the cross-correlation score, as calculated above, for the peaks p1 and p2 illustrated in FIG. 17 would be a positive number because the peaks partially overlap, but would be below a threshold score for recognizing a peak match, since the peaks have different shapes. The cross-correlation score for a peak with itself or with a scaled version of itself is unity. Note from FIG. 15A that, by this measure, the peaks p4 and f4 would have a high cross-correlation score even though they have different magnitudes. In the same fashion, peak p2 would strongly correlate with peak f2 and peak p1 would strongly correlate with peak f1. By contrast, the cross-correlation score between the peaks p3 and p4 illustrated in FIG. 15B would be essentially zero because these peaks have no overlap (every term in the numerator of Eq. 4 would be essentially zero).

The method also may also calculate and include a mass defect correlation. The mass defect is simply the difference, Δm, between the unit resolution mass and the actual mass, expressed in a relative sense such as parts per million (ppm). Thus the mass defect for a peak, p, can be expressed as:

$$MD_p = 1000000 \times \frac{\Delta m_p}{m_p} \quad \text{Eq. 5}$$

FIG. 15C illustrates how the quantities $\Delta m_3$ and $\Delta m_4$ may be determined for the peaks p3 and p4, respectively. Note that the sign of the mass defect is negative for peak p3 and positive for peak p4. The peaks p3 and p4 illustrated in FIG. 15C are the same peaks as illustrated in FIG. 15B, but are shown along the mass axis instead of the orthogonal time axis, as in FIG. 15B. Thus, the mass defect provides an independent measure of the potential relatedness of the peaks. This is true in the broadest sense if one considers the mass defect to arise from numerous small contributions from all the atoms in the structure, and the fragments to be of composition typical to the whole. So, for example, an alkane chain that is fragmented will have the same mass defect (on a relative basis) in both halves. On the other hand, chlorobenzene that is fragmented into benzene and chloride ions will have markedly different mass defects.

The mass defect correlation, $MDC_{(p1,p2)}$, between two peaks p1 and p2, is computed simply as $$MDC_{(p1,p2)} = 1 - A(MD_{p1} - MD_{p2}) \quad \text{Eq. 6}$$

where A is a suitable multiplicative constant. Therefore the mass defect correlation ranges from 1 (exactly the same relative defect) to some small number that depends on the value of A.

If it is desired to also use a peak width correlation, which is calculated by a similar formula, using the absolute peak widths as determined by PPD on the XIC peak shapes. Accordingly, an optional peak width correlation, $PWC_{(p1,p2)}$, between peaks p1 and p2 may be calculated by $$PWC_{(p1,p2)} = 1 - B|width_{p1} - width_{p2}| \quad \text{Eq. 7}$$

in which B is the inverse of the maximum of $width_{p1}$ and $width_{p2}$ and the vertical bars represent the mathematical absolute value operation.

The cross-correlation score, as shown in step 59 of method 40 (FIG. 4A) is calculated by combining the peak-shape correlation score, PSC, together with the mass defect correlation score, MDC, and possibly with the peak width correlation score, PWC, as a weighted average. Accordingly, the overall correlation score, $CCS_{(p1,p2)}$, is given by $$CCS_{(p1,p2)} = \{X[PSC_{(p1,p2)}] + Y[MDC_{(p1,p2)}] + Z[PWC_{(p1,p2)}]\}/\{X+Y+Z\} \quad \text{Eq. 8}$$

in which X, Y and Z are weighting factors. Thus, the overall score, CCS, ranges from 1.0 (perfect match) down to 0.0 (no match). Peak matches are recognized when a correlation exceeds a certain pre-defined threshold value. Experimentally, it is observed that limiting recognized matches to scores to those above 0.90 provides reconstructed MS/MS spectra that match extremely well to experimental spectra.

As one example of how matches recognized from the CSS calculation are used, if a first member of a recognized matched set is a mass from a precursor ion scan, and the list of correlated masses above the 0.90 correlation limit contains 1 additional ion from the precursor ion scan and 4 fragmented ions (in the product ion scan), then 2 potential MS/MS spectra will be reconstructed—one for the first precursor ion mass, and a second for the second precursor ion mass found in the list of correlated masses. For a second example, if the starting mass is found in the product ion scan data and the list of correlated masses contains 4 masses from the precursor ion data and nothing else, then 4 potential MS/MS spectra will be constructed, all having the same product ion but with each having a different precursor mass. It should be pointed out, however, that the actual correlation scores provide a confidence value in the validity of the reconstructed MS/MS spectra, and very often there is a large difference in correlation score between the highest scoring candidate precursor ion and the other candidate precursor ions, making one reconstructed MS2 spectrum easily the most likely correct reconstruction.

It may be noted that since the values of the mass for each scan in the group of scans and intensities that form a chromatographic peak are known, there is the opportunity to do some trend analysis of the values. Consequently it should be possible to correct for linear drifts in the mass values, or a systematic mass shift due to ion intensity.

CONCLUSION

The end result of methods described in the preceding text and associated figures is a general method to detect peaks and identify matches between precursor ions and product ions generated in all-ions LC/MS/MS analyses without user-adjustable parameters. Since it requires no user input, it is suitable for automation, use in high-throughput screening environments or for use by untrained operators.

The newly invented methods described herein have no user-adjustable parameters, and can be run automatically in a post-acquisition step, or implemented in firmware and the new, simplified output files created at acquisition time. Although the described methods are somewhat computationally intensive, they are nonetheless able to process data faster than it is acquired, and so can be done in real time, so as to make automated real-time decisions about the course of subsequent mass spectral scans on a single sample or during a single chromatographic separation. Such real-time (or near-real-time) decision making processes require data buffering since chromatographic peaks are searched for in a moving window of time. For instruments that generate significant chemical noise, the number of unique ions that are transferred into the output data file can be 1000× fewer than in the original data. The newly invented methods also provide a list of components found, with details presented including but not limited to, chromatographic retention time and peak width, ion mass, and signal to noise characteristics.

By using fitted parametric functions to describe the data, problems of normalization and time shifting of data points are totally eliminated, and all peaks may easily be characterized by an array of N values. This greatly simplifies the calculation of the vector dot product between the two shapes.

Computer instructions according to any of the methods described above may be supplied as a computer program product or products tangibly embodied on any form of computer readable medium, such as disk storage, optical storage or electronic memory device, such computer program product or products and storage devices themselves being aspects of the present teachings.

The discussion included in this application is intended to serve as a basic description. Although the invention has been described in accordance with the various embodiments shown and described, one of ordinary skill in the art will readily recognize that there could be variations to the embodiments and those variations would be within the spirit and scope of the present invention. The reader should be aware that the specific discussion may not explicitly describe all embodiments possible; many alternatives are implicit. Accordingly, many modifications may be made by one of ordinary skill in the art without departing from the spirit, scope and essence of the invention. Neither the description nor the terminology is intended to limit the scope of the invention. Any patents, patent applications, patent application publications or other literature mentioned herein are hereby incorporated by reference herein in their respective entirety as if fully set forth herein.

What is claimed is:

1. A method for performing a chromatography—mass spectrometry experiment, comprising:
    (a) repeatedly performing, during a time window of the experiment defining a region of interest, the steps of:
        (a1) introducing, into a mass spectrometer, a sample of ions generated from one or more chemical compounds eluting from a chromatograph;
        (a2) analyzing a first portion of the introduced ions, using a mass analyzer of the mass spectrometer, so as to generate a precursor-ion mass spectrum;
        (a3) fragmenting, in a reaction cell of the mass spectrometer, a second portion of the introduced ions, so as to generate product ions; and
        (a4) analyzing the product ions, using the mass analyzer, so as to generate a product ion mass spectrum, wherein plurality of precursor ion mass spectra and plurality of product ion mass spectra resulting from the repeated performing respectively comprise precursor ion data and product ion data;
    (b) calculating a plurality of extracted ion chromatograms (XICs) for the precursor ion data and the product ion data within the region of interest;
    (c) automatically detecting and characterizing chromatogram peaks within each XIC and automatically generating synthetic analytical fit peaks thereof;
    (d) discarding a subset of the synthetic analytical fit peaks which do not satisfy noise reduction rules;
    (e) performing a respective cross-correlation score calculation between each pair of synthetic analytical fit peaks;
    (f) recognizing matches between precursor ions and product ions based on the cross correlation scores; and
    (g) adjusting the operation of the chromatograph or the mass spectrometer during a subsequent execution of steps (a1) through (a4) during a second, subsequent time window of the experiment, said adjustment based on the automatically recognized matches between precursor ions and product ions.

2. A method as recited in claim 1, wherein the step (d) of discarding a subset of the synthetic analytical peaks which do not satisfy noise reduction rules comprises:

comparing an area, $A_j$, of each synthetic analytical fit peak of each respective XIC to a total area, $\Sigma A$, of the respective XIC;

comparing an intensity, $I_j$, of each synthetic analytical fit peak of each respective XIC to an average peak intensity, $I_{ave}$, of the respective XIC; and discarding synthetic analytical fit peaks for which $(A_j/\Sigma A) < \omega$ or that $(I_j/I_{ave}) < \rho$, in which $\omega$ and $\rho$ are pre-determined constants.

3. A method as recited in claim 1, wherein the step (e) of performing a respective cross-correlation score calculation between each pair of synthetic analytical fit peaks comprises:

calculating a peak shape correlation (PSC) between each pair (p1, p2) of synthetic analytical peak profiles;

calculating a mass defect correlation, $MDC_{(p1,p2)}$, between each pair (p1, p2) of synthetic analytical peak profiles; and calculating an overall correlation score as a weighted sum or weighted average of the peak shape correlation and the mass defect correlation.

4. A method as recited in claim 1, wherein the step (a) of repeatedly performing the steps (a1) through (a4) during a time window defining a region of interest for precursor ion data and product ion data generated by the experiment comprises; repeatedly performing the steps (a1) through (a4) during a time window having a width less than or equal to 1.4 minutes.

5. A method as recited in claim 1, wherein the step (a) of repeatedly performing the steps (a1) through (a4) during a time window defining a region of interest comprises repeatedly performing the steps (a1) through (a4) during a time window having a width less than or equal to 0.5 minutes.

6. A method as recited in claim 1, wherein the step (a) of repeatedly performing the steps (a1) through (a4) during a time window defining a region of interest comprises repeatedly performing the steps (a1) through (a4) during a time window having a width equal to 0.2 minutes.

7. A method as recited in claim 1, wherein the step (a) of adjusting the operation of the chromatograph or the mass spectrometer during a subsequent execution of steps (a1) through (a4) during a second, subsequent time window of the experiment comprises adjusting operation of an ion source or adjusting a collision energy that is applied to ions during the second time window so as to optimize the type or number of ions or ion fragments produced during the second time window.

8. A method as recited in claim 1, further comprising eliminating matches between precursor ions and product ions that do not correspond to a valid chemical formula.

9. A method as recited in claim 1, further comprising:

storing information regarding the synthetic analytical fit peaks or the recognized matches between precursor and product ions to a data storage medium.

10. A method as recited in claim 1, wherein the step (e) of performing a respective cross-correlation score calculation between each pair of synthetic analytical fit peaks includes calculating a peak shape correlation (PSC) between each pair (p1, p2) of synthetic analytical peak profiles.

11. A method as recited in claim 10, wherein the peak shape correlation (PSC) between each pair (p1, p2) of synthetic analytical peak profiles is calculated as $$PSC(p1, p2) = \frac{\sum_{j=jmin}^{j=jmax}[p1(t_j) \times p2(t_j)]}{\left\{\sum_{j=jmin}^{j=jmax} p1(t_j)^2\right\}^{1/2} \left\{\sum_{j=jmin}^{j=jmax} p2(t_j)^2\right\}^{1/2}}$$

in which $p1(t_j)$ and $p2(t_j)$ are the values of the synthetic analytical peak profiles, p1 and p2, respectively, at each $j^{th}$ time point and wherein j min and j max are defined lower and upper indices, respectively.

12. A method as recited in claim 1, wherein the step (e) of performing a respective cross-correlation score calculation between each pair of synthetic analytical fit peaks includes calculating a mass defect correlation, $MDC_{(p1,p2)}$, between each pair (p1, p2) of synthetic analytical peak profiles, wherein the mass defect, $MD_p$, in parts per million, for any peak profile, p, is given as $$MD_p = 1000000 \times \frac{\Delta m_p}{m_p}$$

in which $m_p$ is a measured mass associated with the peak profile and $\Delta m_p$ is the difference between the measured mass and unit resolution mass.

13. A method as recited in claim 12, wherein the mass defect correlation between each pair of synthetic analytical peak profiles is calculated as $$MDC_{(p1,p2)} = 1 - A(MD_{p1} - MD_{p2})$$

in which A is a pre-determined constant.

14. An apparatus comprising:

a chromatograph for providing a stream of separated chemical substances;

a mass spectrometer fluidically coupled to the chromatograph for generating a plurality of precursor ions from each separated chemical substance and a plurality of product ions resulting from simultaneous fragmentation of each of the precursor ions;

a detector for detecting abundance data for each product ion and each product ion; and a programmable electronic processor electrically coupled to the mass spectrometer, the chromatograph and the detector, the programmable processor comprising instructions operable to cause the programmable processor to:

receive the abundance data for each of the product ions and precursor ions detected by the detector during a time window;

automatically detect and characterize chromatogram peaks as a function of time for each of a plurality of mass-to-charge ratio ranges of the abundance data for the product ions and precursor ions;

automatically generate synthetic analytical fit peaks to the detected chromatogram peaks;

automatically discard a subset of the synthetic analytical fit peaks which do not satisfy noise reduction rules;

automatically perform a respective cross-correlation score calculation between each pair of synthetic analytical fit peaks; and automatically recognize matches between precursor ions and product ions based on the cross correlation scores.

15. An apparatus as recited in claim 14, wherein the instructions are further operable to cause the programmable processor to:
   adjust operation of the chromatograph or the mass spectrometer during generation of a second plurality of precursor ions and a second plurality of product ions during a second, subsequent time window, said adjustment based on the automatically recognized matches between precursor ions and product ions.

16. An apparatus as recited in claim 14, wherein the instructions operable to cause the programmable processor to adjust operation of the chromatograph or the mass spectrometer during generation of the second pluralities of precursor and product ions during a second, subsequent time window are operable to adjust a voltage of an ion source of the mass spectrometer during generation of the second plurality of precursor ions or to adjust a collision energy applied to the second plurality of precursor ions.

17. An apparatus as recited in claim 14, wherein the instructions are further operable to cause the programmable processor to:
   store information regarding the synthetic analytical fit peaks or the recognized matches between precursor and product ions to a data storage medium.

18. An apparatus as recited in claim 14, wherein the instructions operable to cause the programmable processor to automatically perform a respective cross-correlation score calculation between each pair of synthetic analytical fit peaks are operable to cause the programmable processor to perform at least one of a peak shape cross correlation calculation, a mass defect correlation calculation and a peak width correlation calculation.

19. An apparatus as recited in claim 14, wherein the instructions operable to cause the programmable processor to automatically detect and characterize chromatogram peaks as a function of time is operable to cause the programmable processor to automatically detect and characterize the chromatogram peaks as a function of time in the absence of any user input parameters.

* * * * *

UNITED STATES PATENT AND TRADEMARK OFFICE
CERTIFICATE OF CORRECTION

PATENT NO. : 8,935,101 B2  
APPLICATION NO. : 12/970570  
DATED : January 13, 2015  
INVENTOR(S) : David A. Wright Page 1 of 1

It is certified that error appears in the above-identified patent and that said Letters Patent is hereby corrected as shown below:

In the claims

Claim 4, column 29, line 26-28:  
replace "… a region of interest for precursor ion data and product ion data generated by the experiment comprises; …"  
with --… a region of interest comprises …--

Claim 7, column 29, line 42:  
replace "…, wherein the step (a) of …"  
with --…, wherein the step (g) of …--

Signed and Sealed this  
Third Day of May, 2016

Michelle K. Lee  
*Director of the United States Patent and Trademark Office*